(12) United States Patent
Gibson

(10) Patent No.: US 11,426,576 B2
(45) Date of Patent: *Aug. 30, 2022

(54) SECURING AN IMPLANTED MEDICAL DEVICE IN A PATIENT

(71) Applicant: Cochlear Limited, Macquarie University (AU)

(72) Inventor: Peter Gibson, South Coogee (AU)

(73) Assignee: Cochlear Limited, Macquarie University (AU)

( * ) Notice: Subject to any disclaimer, the term of this patent is extended or adjusted under 35 U.S.C. 154(b) by 34 days.

This patent is subject to a terminal disclaimer.

(21) Appl. No.: 16/882,582

(22) Filed: May 25, 2020

(65) Prior Publication Data

US 2020/0384263 A1    Dec. 10, 2020

Related U.S. Application Data

(63) Continuation of application No. 15/846,533, filed on Dec. 19, 2017, now Pat. No. 10,661,076, which is a continuation of application No. 15/218,585, filed on Jul. 25, 2016, now Pat. No. 10,022,535, which is a continuation of application No. 12/052,193, filed on Mar. 20, 2008, now Pat. No. 9,402,990.

(60) Provisional application No. 60/918,917, filed on Mar. 20, 2007.

(51) Int. Cl.
*A61N 1/05* (2006.01)
*A61N 1/372* (2006.01)

(52) U.S. Cl.
CPC ........... *A61N 1/0541* (2013.01); *A61N 1/372* (2013.01)

(58) Field of Classification Search
CPC ................................ A61N 1/0541; A61N 1/37
See application file for complete search history.

(56) References Cited

U.S. PATENT DOCUMENTS

| 3,819,875 A | 6/1974 | Velmans |
| 4,261,372 A | 4/1981 | Hansen et al. |
| 4,487,210 A | 12/1984 | Knudsen et al. |
| 4,532,930 A | 8/1985 | Crosby et al. |

(Continued)

FOREIGN PATENT DOCUMENTS

| AU | 2005201999 A1 | 11/2005 |
| AU | 2005203696 A1 | 11/2005 |

(Continued)

OTHER PUBLICATIONS

Austrian Office Action dated Nov. 4, 2010, issued in connection with Austrian Patent Application No. A 576/2009, and partial English-language translation of the Office Action.

(Continued)

*Primary Examiner* — Catherine M Voorhees
(74) *Attorney, Agent, or Firm* — Pilloff Passino & Cosenza LLP; Martin J. Cosenza

(57) ABSTRACT

An apparatus and method for implanting and securing an implanted medical device in a recipient. The implantable medical device of the generally includes an electrode assembly that comprises an elongate carrier member having at least one stimulating electrode positioned thereon. The carrier member further has a fixation structure positioned thereon configured to interact with a portion of the rigid structure to longitudinally secure the carrier member in the recipient.

19 Claims, 15 Drawing Sheets

(56) References Cited

U.S. PATENT DOCUMENTS

| | | | |
|---|---|---|---|
| 4,608,057 A | 8/1986 | Davis et al. | |
| 4,645,504 A * | 2/1987 | Byers | A61F 2/00 |
| | | | 623/10 |
| 4,706,682 A | 11/1987 | Stypulkowski et al. | |
| 4,795,426 A | 1/1989 | Jones | |
| 4,892,108 A | 1/1990 | Miller et al. | |
| 4,898,183 A | 2/1990 | Kuzma | |
| 4,957,478 A | 9/1990 | Maniglia | |
| 5,143,090 A | 9/1992 | Dutcher et al. | |
| 5,267,968 A | 12/1993 | Russo | |
| 5,594,174 A | 1/1997 | Keefe | |
| 5,626,629 A | 5/1997 | Faltys et al. | |
| 5,758,651 A | 6/1998 | Nygard et al. | |
| 5,776,179 A | 7/1998 | Ren et al. | |
| 5,782,744 A | 7/1998 | Money | |
| 5,792,072 A | 8/1998 | Keefe | |
| 5,922,017 A | 7/1999 | Bredberg et al. | |
| 5,991,663 A | 11/1999 | Irlicht et al. | |
| 6,070,105 A | 5/2000 | Kuzma | |
| 6,119,044 A | 9/2000 | Kuzma | |
| 6,151,526 A | 11/2000 | Tziviskos | |
| 6,157,861 A | 12/2000 | Faltys et al. | |
| 6,163,729 A | 12/2000 | Kuzma | |
| 6,231,604 B1 | 5/2001 | von Ilberg | |
| 6,259,951 B1 | 7/2001 | Kuzma et al. | |
| 6,308,101 B1 | 10/2001 | Faltys et al. | |
| 6,321,125 B1 * | 11/2001 | Kuzma | A61N 1/0541 |
| | | | 607/137 |
| 6,415,185 B1 | 7/2002 | Maltan | |
| 6,487,453 B1 | 11/2002 | Kuzma et al. | |
| 6,498,954 B1 | 12/2002 | Kuzma et al. | |
| 6,537,200 B2 | 3/2003 | Leysieffer et al. | |
| 6,556,870 B2 | 4/2003 | Zierhofer et al. | |
| 6,565,503 B2 | 5/2003 | Leysieffer et al. | |
| 6,575,894 B2 | 6/2003 | Leysieffer et al. | |
| 6,628,991 B2 | 9/2003 | Kuzma et al. | |
| 6,697,674 B2 | 2/2004 | Leysieffer | |
| 6,754,537 B1 | 6/2004 | Harrison et al. | |
| 6,889,094 B1 * | 5/2005 | Kuzma | A61N 1/0541 |
| | | | 607/137 |
| 6,915,166 B1 | 7/2005 | Stecker et al. | |
| 7,050,858 B1 | 5/2006 | Kuzma et al. | |
| 7,146,227 B2 | 12/2006 | Dadd et al. | |
| 7,194,314 B1 * | 3/2007 | Richter | A61N 1/0541 |
| | | | 607/57 |
| 7,239,069 B2 | 7/2007 | Cho | |
| 7,346,397 B2 | 3/2008 | Money et al. | |
| 7,451,000 B2 | 11/2008 | Gibson et al. | |
| 7,460,913 B2 | 12/2008 | Kuzma et al. | |
| 7,966,077 B2 | 6/2011 | Risi | |
| 8,718,795 B2 * | 5/2014 | Gibson | A61N 1/372 |
| | | | 607/137 |
| 8,874,239 B2 | 10/2014 | Greenberg et al. | |
| 9,402,990 B2 * | 8/2016 | Gibson | A61N 1/0541 |
| 10,661,076 B2 * | 5/2020 | Gibson | A61N 1/0541 |
| 2002/0156513 A1 | 10/2002 | Borkan | |
| 2003/0078516 A1 | 4/2003 | Abbasi et al. | |
| 2003/0097121 A1 | 5/2003 | Jolly et al. | |
| 2004/0133250 A1 | 7/2004 | Ball et al. | |
| 2004/0225336 A1 | 11/2004 | Milojevic et al. | |
| 2004/0236390 A1 | 11/2004 | Dadd et al. | |
| 2005/0101878 A1 | 5/2005 | Daly et al. | |
| 2005/0139016 A1 | 6/2005 | Yamanaka et al. | |
| 2005/0240147 A1 | 10/2005 | Makower et al. | |
| 2005/0245991 A1 | 11/2005 | Faltys et al. | |
| 2005/0256561 A1 | 11/2005 | Gantz et al. | |
| 2005/0261748 A1 | 11/2005 | van Dijk | |
| 2006/0079950 A1 | 4/2006 | Lehnhardt et al. | |
| 2006/0116743 A1 | 6/2006 | Gibson et al. | |
| 2006/0287689 A1 | 12/2006 | Debruyne et al. | |
| 2006/0287690 A1 | 12/2006 | Bouchataoui et al. | |
| 2007/0135884 A1 | 6/2007 | Risi | |
| 2007/0162098 A1 * | 7/2007 | Risi | A61N 1/0541 |
| | | | 607/137 |
| 2007/0179566 A1 | 8/2007 | Gantz et al. | |
| 2007/0203557 A1 | 8/2007 | Gantz et al. | |
| 2008/0154339 A1 | 6/2008 | Carter | |
| 2008/0215053 A1 | 9/2008 | Thomke et al. | |
| 2008/0234793 A1 | 9/2008 | Gibson | |
| 2009/0254163 A1 | 10/2009 | Gibson | |

FOREIGN PATENT DOCUMENTS

| | | |
|---|---|---|
| AU | 2006252212 A1 | 7/2007 |
| EP | 0884991 B1 | 7/2005 |
| EP | 1972359 A2 | 9/2008 |
| WO | 9631087 A1 | 10/1996 |
| WO | 9726943 A1 | 7/1997 |
| WO | 0069513 A1 | 11/2000 |
| WO | 00071063 A1 | 11/2000 |
| WO | 02082982 A1 | 10/2002 |
| WO | 2002078575 A1 | 10/2002 |
| WO | 2003024153 A1 | 3/2003 |
| WO | 2004004413 A1 | 1/2004 |

OTHER PUBLICATIONS

Balkany et al., "Fixation of the Electrode Cable During Cochlear Implantation: The Split Bridge Technique," Laryngoscope 105: Feb. 1995, pp. 2317-218.

Digisonic Convex Receiver document, believed to have been available as of late 2003.

Extended European Search Report issued in connection with European Patent Application No. 08005372, dated Dec. 12, 2008.

Cohen, "Surgical Techniques for Cochlear Implants", Cochlear Implants, edited by Waltzman et al., Thieme New York, 2000, pp. 151-169, Chapter 8.

Cohen, "Titanium Clip for Cochlear Implant Electrode Fixation," Clark et al., International Cochlear Implant, Speech and Hearing Symposium, Melbourne 1994; Annals of Otology, Rhinology & Laryngology, vol. 104, No. 9, Part 2, Supplement 166, Sep. 1995, pp. 402-403.

Gibson, Abstract for "Electrode Design Considerations for Reducing Trauma", 9th International Conference on Cochlear Implants and Related Sciences, Jun. 15, Vienna, Austria 2006.

Gibson, et al., "Electrode Design Considerations for Reducing Trauma", 9th International Conference on Cochlear Implants and Related Sciences, Jun. 14-17, Vienna, Austria 2006.

Lenarz, et al., "Hearing Conservation Surgery Using the Hybrid-L Electrode", Audiology and Neurotology, Apr. 2009, 14(1); pp. 22-31.

Lenarz, Abstract for "Preservation of Residual Hearing with a New Straight Electrode", Jun. 14-17, 2006, Wiener Medizinische Wochenschrift, Abstracts, 2006, pp. 126-127 2006.

Lenarz, et al., "Temporal Bone Results and Hearing Preservation with a New Straight Electrode", presented at Cochlear Implantation, 1st International Electro-Acoustic Workshop, Toulouse, Dec. 8-10, 2005, published at Audiol Neurotol 2006; 11 (suppl 1), pp. 34-41, Oct. 6, 2006.

Lenarz, "Temporal Bone Results and Hearing Conservation with a New Straight Electrode", presented at 1st International Electro-Acoustic Workshop, Toulouse, Dec. 8-10, 2005.

Xu et al., "Temporal Bone Surgical Dissection for Cochlear Implantation," for Nucleus Freedom and Nucleus 24 Implants, send to printers in late 2005.

Bruce J. Gantz et al., "Combining Acoustic and Electrical Hearing", Laryngoscope, 113: Oct. 2003, pp. 1726-1730.

European Communication dated May 16, 2011 for European Application No. 08005372.1.

Austrian Office Action dated Jun. 20, 2011 for Austrian Application No. 576/2009.

International Search Report for PCT/AU03/00828 dated Sep. 2, 2003.

International Preliminary Examination Report for PCT/AU03/00828 dated Oct. 8, 2004.

Written Opinion for PCT/AU03/00828 dated Oct. 16, 2003.

(56) References Cited

OTHER PUBLICATIONS

T. Lenarz, "Introduction of Surgical Concepts", Dept. of Otolaryngology, Medical University of Hannover, 1st Hybrid-L Workshop, Jun. 13, 2006.

* cited by examiner

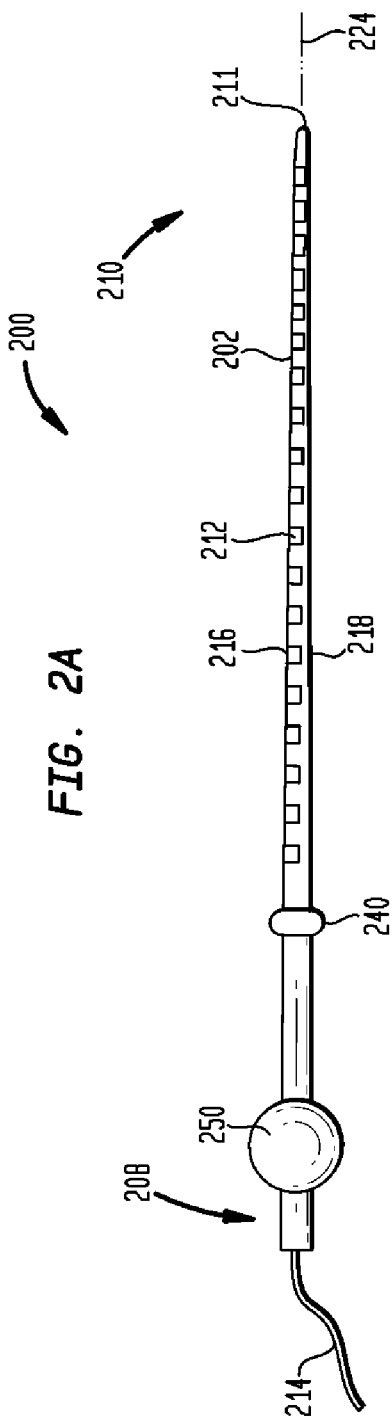

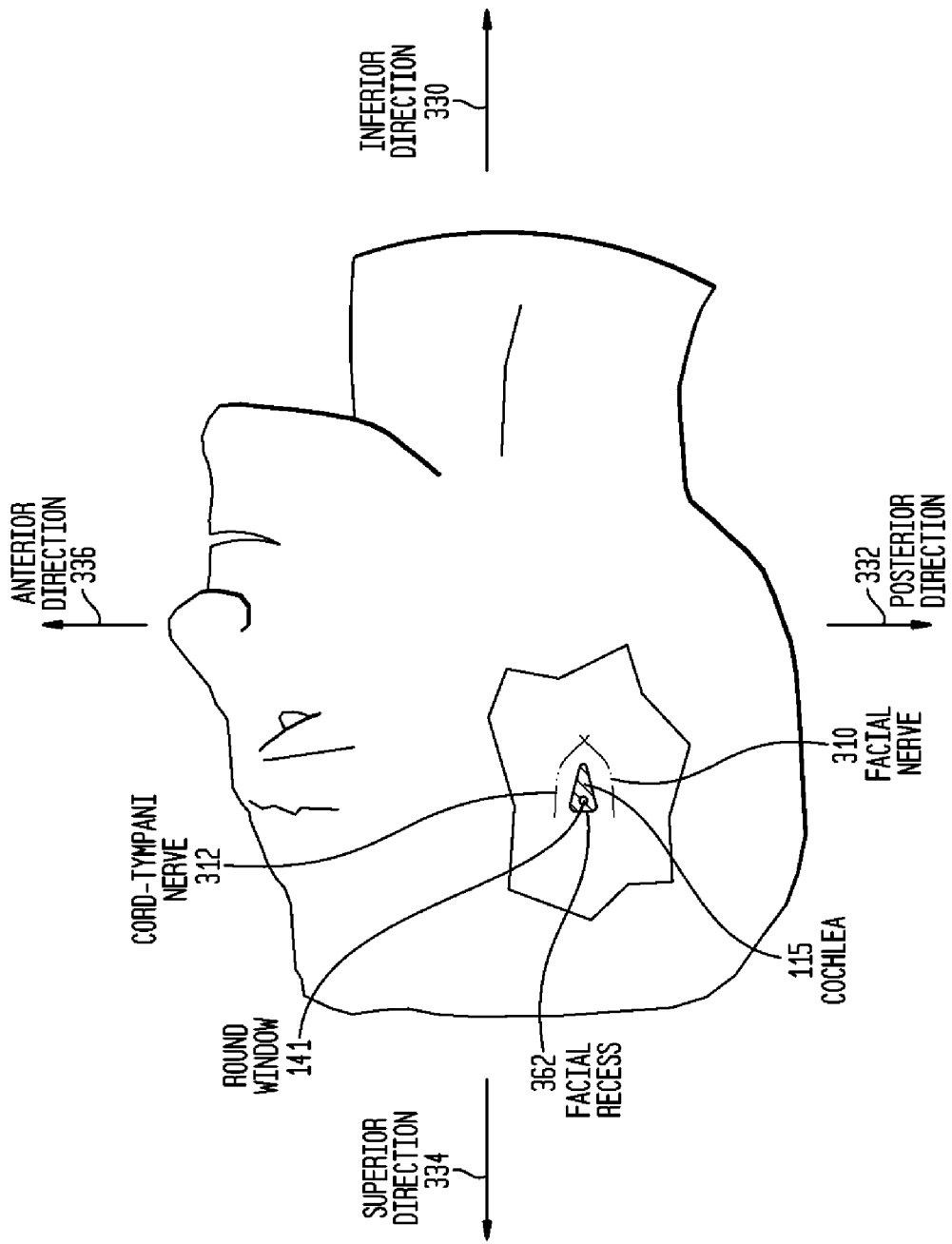

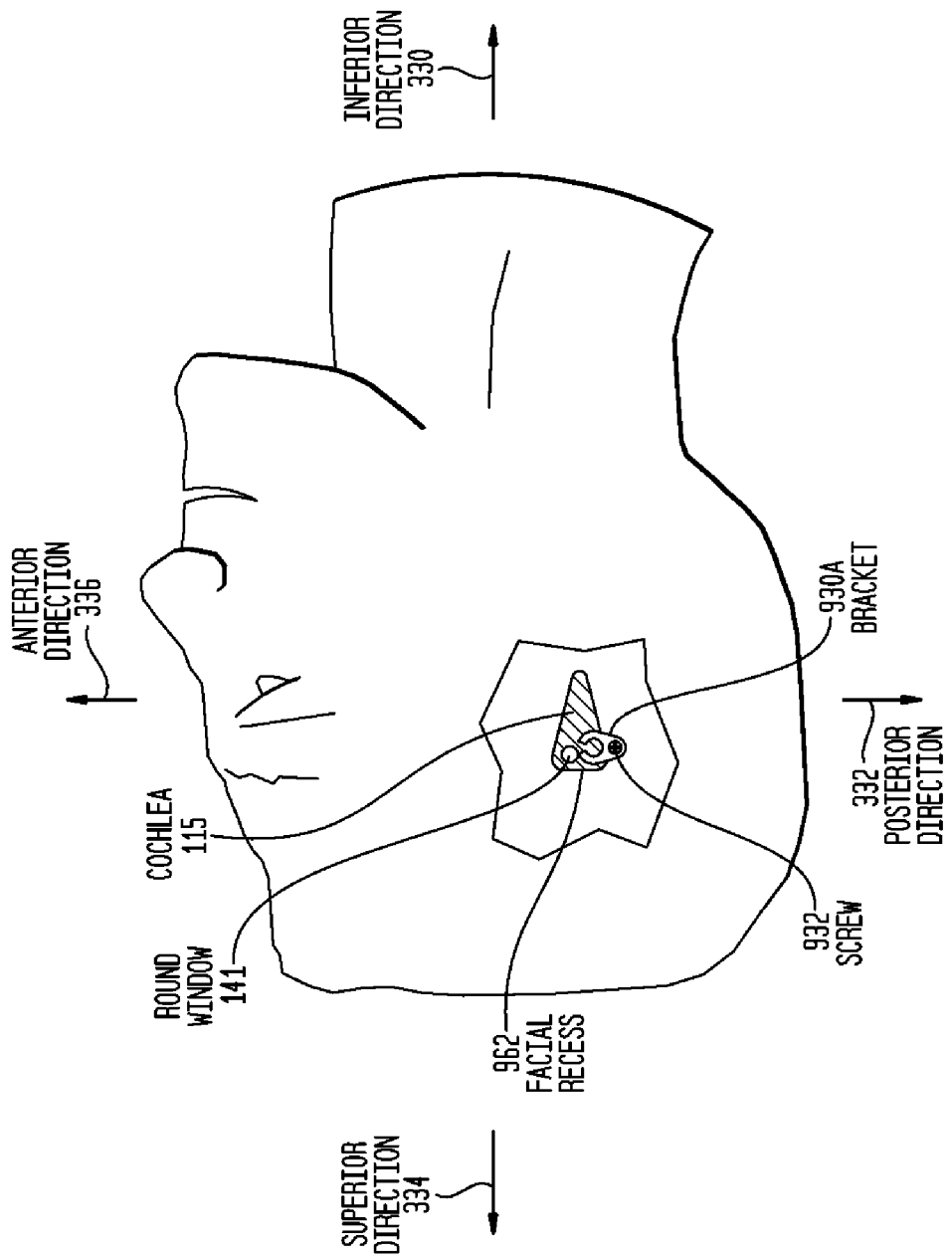

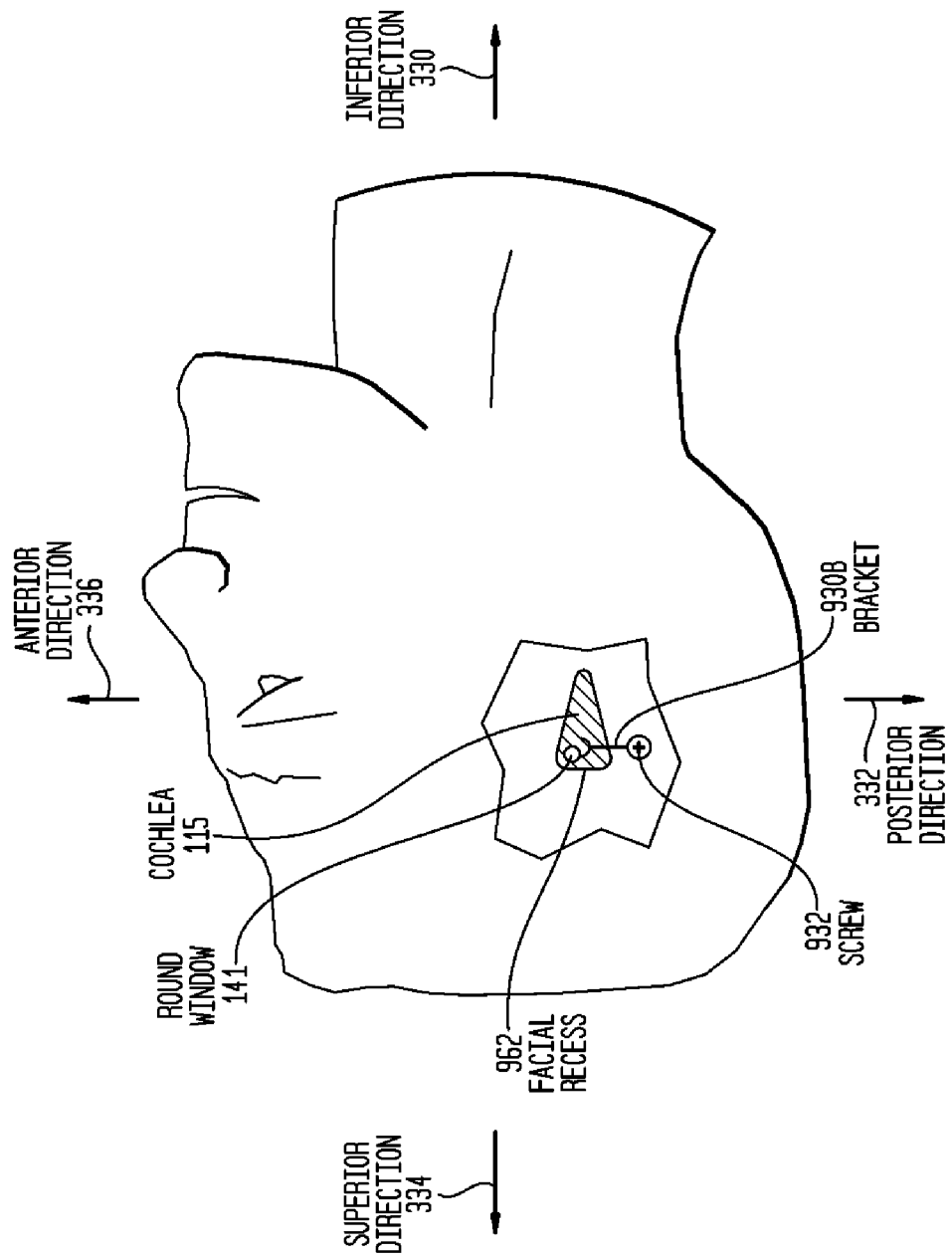

SECURING AN IMPLANTED MEDICAL DEVICE IN A PATIENT

CROSS-REFERENCE TO RELATED APPLICATIONS

The present application is a Continuation application of U.S. patent application Ser. No. 15/846,533, filed Dec. 19, 2017, naming Peter Gibson as an inventor, which is a Continuation application of U.S. patent application Ser. No. 15/218,585, filed Jul. 25, 2016, now U.S. Pat. No. 10,022,535, which is a Continuation application of U.S. patent application Ser. No. 12/052,193, filed Mar. 20, 2008, now U.S. Pat. No. 9,402,990, which claims priority to U.S. Provisional application No. 60/918,917, filed Mar. 20, 2007. The entire contents of these applications are incorporated herein by reference in their entirety.

BACKGROUND

Field of the Invention

The present invention relates generally to medical devices, and more particularly, to securing an implanted medical device in a patient.

Related Art

Hearing loss is generally of two types, namely conductive and sensorineural. The treatment of both types of hearing loss has been quite different, relying on different principles to enable sound percepts to be generated in a recipient's brain. Conductive hearing loss occurs when the normal mechanical pathways for sound to reach the hair cells in the cochlea are impeded, for example, by damage to the ossicles. In such cases, hearing is often improved with the use of conventional hearing aids. Such hearing aids amplify sound so that acoustic information reaches the hair cells of the cochlea. Typically, conventional hearing aids utilize acoustic mechanical stimulation, whereby the sound is amplified according to a number of varying techniques, and delivered to the inner ear as mechanical energy. This may be, for example, through a column of air to the eardrum, or through direct delivery to the ossicles of the middle ear.

Sensorineural hearing loss is due to the absence or destruction of the cochlear hair cells which are needed to transduce acoustic signals into auditory nerve impulses. Individuals suffering from this type of hearing loss are unable to derive any benefit from conventional hearing aids regardless of the magnitude of the acoustic mechanical stimulus. In such cases, Cochlear™ implants (also referred to as Cochlear™ devices, Cochlear™ prostheses, Cochlear™ implant systems, and the like; simply "cochlear implants" herein) have been developed to provide hearing percepts to such individuals. Cochlear implants provide electrical stimulation via stimulating electrodes positioned as close as possible to the nerve endings of the auditory nerve, essentially bypassing the cochlear hair cells. The application of a stimulation pattern to the nerve endings causes impulses to be sent to the brain via the auditory nerve, resulting in the brain perceiving the impulses as sound.

It is relatively common for some hearing impaired individuals to experience profound hearing loss for high frequency sounds, and yet still be able to discern middle-to-low frequency sounds. Traditionally, such individuals typically do not receive a cochlear implant, as noted above, due to the potential trauma caused by the implantation of a traditional electrode assembly into the cochlea. Rather, in the majority of such cases, such an individual receives treatment to preserve and improve hearing in the middle-to-low frequency range, typically via a conventional hearing aid. Minimal effort would be expended to restore hearing in the high frequency range. Unfortunately, such individuals generally experience poor restoration of their hearing with conventional hearing aids alone.

Recently, there has been an increased interest in assisting individuals with residual hearing who do not experience adequate restoration from conventional hearing aids alone. One proposed approach for assisting these individuals is through the use of Electro-Acoustical Stimulation (EAS). So called EAS devices provide electrical stimulation of the cochlea in conjunction with acoustical stimulation.

SUMMARY

In one aspect of the invention, an electrode assembly for implantation into a recipient through an opening in a reference structure in the recipient, comprising: an elongate carrier member, having proximal and a distal ends and at least one electrode disposed along the carrier member; and an integrated fixation structure constructed and arranged to interact with the reference structure to when the carrier member is implanted in the recipient, wherein the interaction prevents substantial translation of the carrier member.

In another aspect of the invention, a method of implanting a stimulating medical device, comprising: preparing an appropriately configured opening in an internal reference structure of a recipient for implantation of an elongate carrier member therethrough; inserting the carrier member through the opening in the recipient; and allowing a fixation structure positioned on the carrier member to interact with a portion of the structure to longitudinally secure the carrier member in the recipient.

BRIEF DESCRIPTION OF THE DRAWINGS

Illustrative embodiments of the present invention are described herein with reference to the accompanying figures, in which:

FIG. 2A is a side view of an electrode assembly in accordance with one embodiment of the present invention shown prior to insertion into a cochlea;

FIG. 3 is a perspective view of a recipient illustrating the location of implantation of an electrode assembly in accordance with embodiments of the present invention;

FIG. 9A is a perspective view of a recipient illustrating the location and orientation of a bracket used to cooperate with embodiments of the present invention;

FIG. 9B is a partial cross-sectional view of a recipient illustrating the location and orientation of another bracket used to cooperate with embodiments of the present invention.

DETAILED DESCRIPTION

Embodiments of the present invention are generally directed to securing an implantable medical device in a patient (also referred to as a recipient). Certain embodiments are described herein in connection with one type of implantable medical device, a prosthetic hearing implant and, more specifically, a cochlear implant. Cochlear implants use direct electrical stimulation of auditory nerve cells to bypass absent or defective hair cells that normally transduce acoustic vibrations into neural activity. Such devices generally use multi-contact electrodes inserted into the scala tympani of the cochlea so that the electrodes may differentially activate auditory neurons that normally encode differential pitches of sound. These devices are also used to treat a smaller number of recipients with bilateral degeneration of the auditory nerve. Such devices are described in commonly owned and co-pending U.S. patent application Ser. Nos. 11/605,952 and 11/605,951, which are hereby incorporated by reference herein. For such recipients, a cochlear implant provides stimulation of the cochlear nucleus in the brainstem. Such devices, therefore, are commonly referred to as auditory brainstem implants (ABIs).

Although some embodiment of the present invention are described herein with reference to a particular type of cochlear implant, it should be understood that embodiments of the present invention may be implemented in connection with all forms of cochlear implants. Furthermore, it should be understood by those of ordinary skill in the art that embodiments of the present invention may be implemented in stimulating medical devices other than cochlear implants such as neurostimulators, cardiac pacemakers defibrillators, etc. as well as other medical devices which utilize a carrier member to temporarily or permanently implant, deliver or otherwise introduce into a recipient a therapeutic agent, sensor, electrodes or other active or passive components now or later developed.

Exemplary embodiments of a cochlear implant utilized in accordance with embodiments of the present invention include a Contour™, Freedom™, Nucleus™ or Cochlear™ implant sold by Cochlear Limited, Australia. Such devices are described in U.S. Pat. Nos. 4,532,930, 6,537,200, 6,565,503, 6,575,894, and 6,697,674, which are hereby incorporated by reference herein. Similarly, cochlear implants utilizing a short electrode array are described in commonly owned and co-pending U.S. patent application Ser. Nos. 11/605,952 and 11/605,951, which are hereby incorporated by reference herein.

Figure 1:
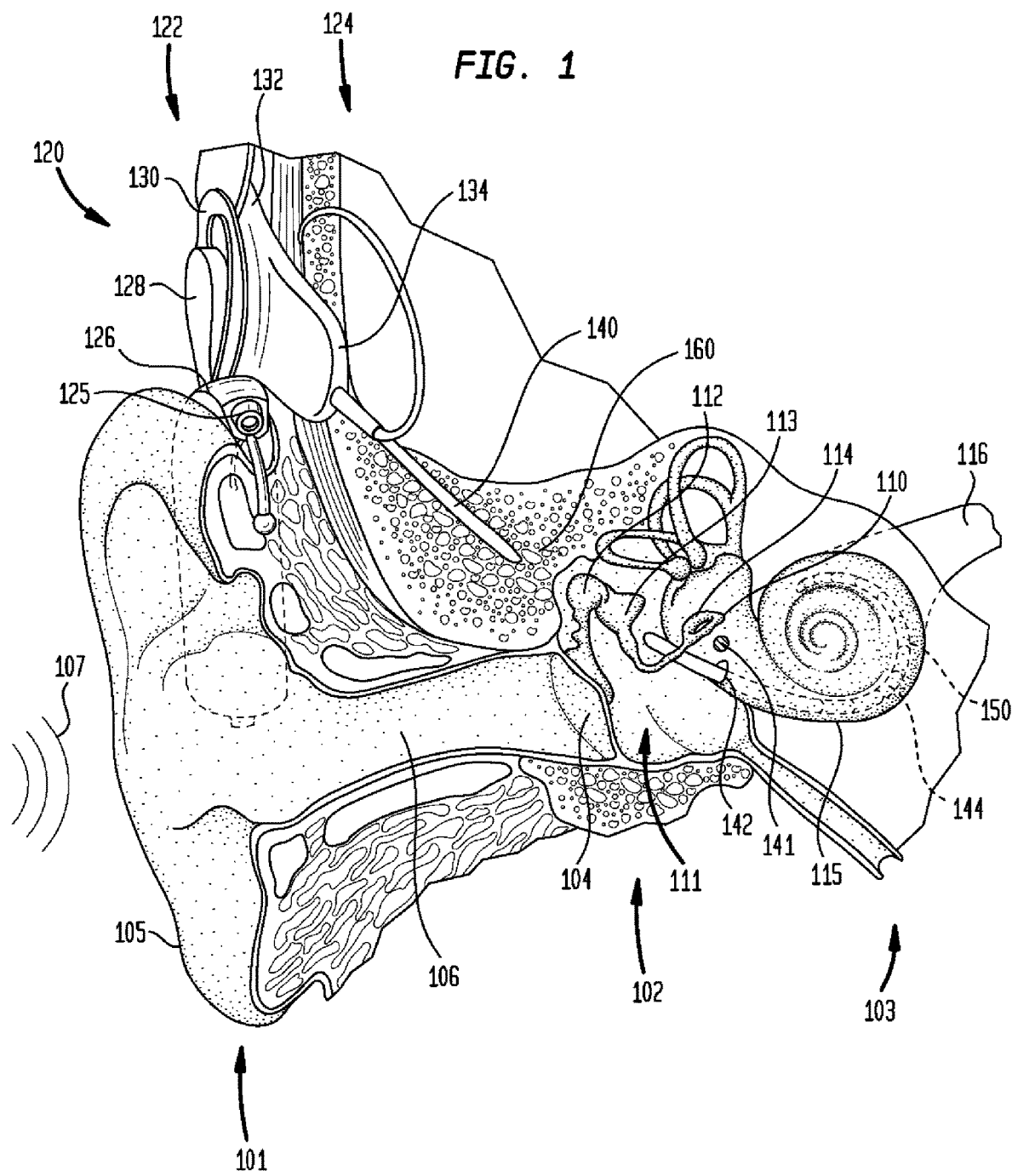
FIG. 1 is a perspective view of an example of an implanted cochlear implant suitable for implementing embodiments of the present invention.

FIG. 1 is a cut-away view of the relevant components of outer ear 101, middle ear 102 and inner ear 103, with an exemplary cochlear implant 120. In a fully functional ear, outer ear 101 comprises an auricle 105 and an ear canal 106. An acoustic pressure or sound wave 107 is collected by auricle 105 and channeled into and through ear canal 106. Disposed across the distal end of ear cannel 106 is a tympanic membrane 104 which vibrates in response to acoustic wave 107. This vibration is coupled to oval window, or fenestra ovalis, 110 through three bones of middle ear 102, collectively referred to as the ossicles 111.

Ossicles 111 comprise malleus 112, incus 113 and stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells (not shown) to auditory nerve 116 and, ultimately, to the brain where they are perceived as sound. In some persons experiencing sensorineural hearing loss, there is an absence or destruction of the hair cells. Cochlear implant 120 is utilized to directly stimulate the ganglion cells to provide a hearing sensation to such persons.

FIG. 1 also shows how cochlear implant 120 is positioned in relation to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is provided to a behind-the-ear (BTE) speech processing unit 126 that generates coded signals. The coded signals are provided to an external transmitter unit 128, along with power from a power source (not shown) such as a battery. External transmitter unit 128 comprises an external coil 130 and, preferably, a magnet (not shown) secured directly or indirectly in external coil 130.

Internal component assembly 124 comprises an internal receiver unit 132 having an internal coil (not shown) that transcutaneously receives power and coded signals from external assembly 122, and provides such signals to a stimulator unit 134. In response to the coded signals, stimulator 134 applies stimulation signals to cochlea 115 via an electrode assembly 140 implanted through temporal bone 160. Electrode assembly 140 enters cochlea 115 via an opening of the perilymphatic spaces of cochlea 115, referred to as cochleostomy 142, and has an array 144 of one or more electrodes 150 positioned to be substantially aligned with portions of tonotopically-mapped cochlea 115. The delivery of stimulation signals at various locations along cochlea 115 causes a hearing percept representative of the received sound 107.

While cochlear implant 120 is described as having external components, in another embodiment, the controller, including the microphone, speech processor and power supply, may also be implantable. In such embodiments, the controller may be contained within a hermetically sealed housing or the housing used for stimulator unit 134.

Electrode assembly 140 preferably assumes an optimal electrode position in cochlea 115 upon or immediately following implantation into the cochlea. It is also desirable that electrode assembly 140 be configured such that the insertion process causes minimal trauma to the sensitive structures of cochlea 115. Typically, electrode assembly 140 is pre-curved, held in a substantially straight configuration at least during the initial stages of the implantation procedure, then conforming to the natural shape of the cochlea during, and subsequent to, implantation.

Figure 2B:
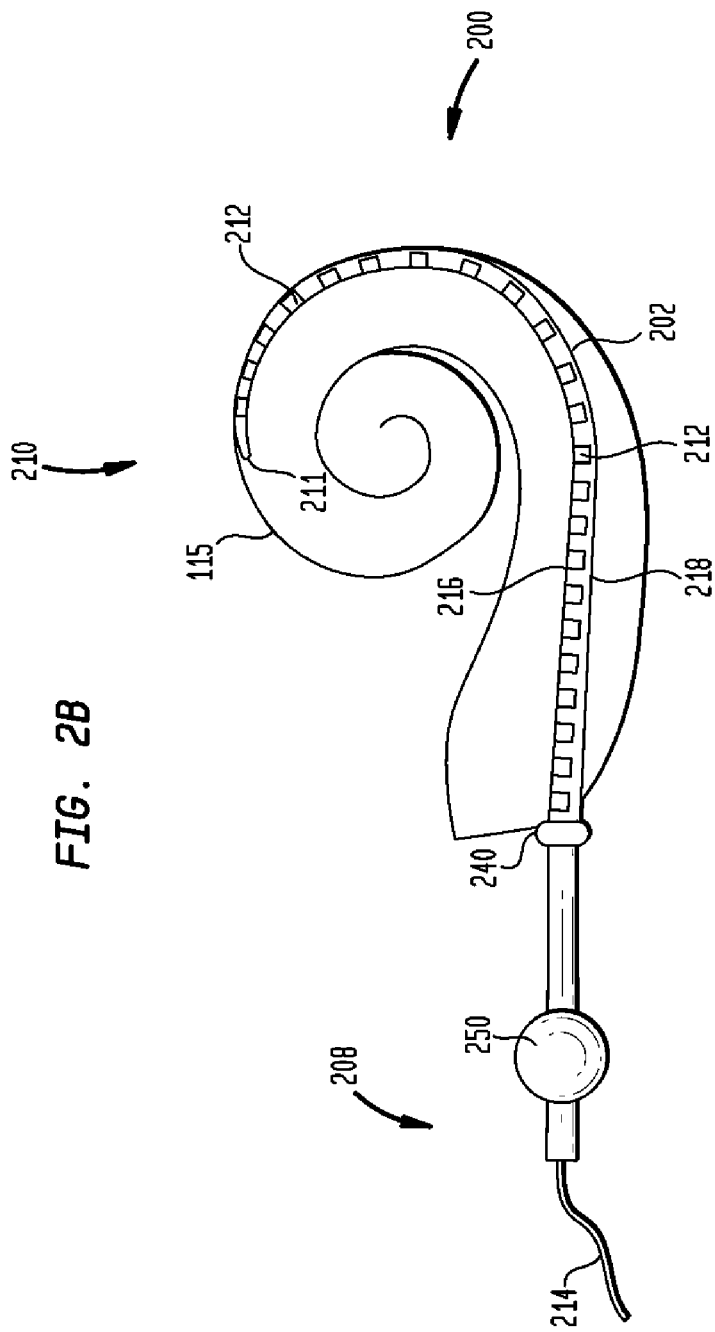
FIG. 2B is a side view of the electrode assembly illustrated in FIG. 2A, shown inserted into a cochlea.

FIGS. 2A and 2B are side views of an embodiment of electrode assembly 140, referred to herein as electrode assembly 200. In FIG. 2A, the electrode assembly is illustrated prior to insertion in a recipient's cochlea; FIG. 2B, following insertion. Electrode assembly 200 comprises a carrier member 202 having a proximal end 208 and a distal end 210. Distal end 210 terminates in tip 211, and is adapted to be implanted furthest into cochlea 115. A plurality of spaced-apart electrodes 212 are mounted or disposed on or in carrier member 202. Electrodes 212 are embodiments of electrodes 144 (FIG. 1). It should be appreciated that as used herein, particular combinations of the terms mounted/disposed, in/on, etc., are not to be interpreted to refer to any particular manufacturing technique or structural relationship.

Attached to or integral with carrier member 202 are a stop member 240 and a fixation structure 250. Fixation structure 250 is positioned on carrier member 202 at or near proximal end 208 of carrier member 202. Fixation structure 250 is described in greater detail below with reference to FIGS. 4-10. Stop member 240 is positioned on carrier member 202 between fixation structure 250 and all, and, in embodiments in which not all electrodes 212 are to be inserted into cochlea 115, some of the electrodes.

Extending from proximal end 208 of carrier member 202 is a lead 214. Lead 214 physically and electrically connects electrode assembly 200 with stimulator unit 134 (FIG. 1).

As shown in FIG. 2B, carrier member 202 may be implanted into cochlea 115 through an aperture in the cochlea. The aperture may be oval window 110, round window 141 or a surgical incision 142. In this description, reference will be made to round window 141 (FIG. 1); it should be appreciated, however, that other embodiments of the present invention may be configured to be implanted in oval window 110 or other natural or man-made aperture in cochlea 115. Carrier member 202 is inserted into cochlea 115 until stop member 240 contacts an exterior surface of cochlea 115 surrounding round window 141. when Abutting cochlea 115 member 240 at least partially prevents perilymphatic fluid from escaping from cochlea 115.

When implanted, the surface of carrier member 202 which faces the interior of cochlea 115 is referred to herein as the medial surface 216 of carrier member 202. The opposing side of carrier member 202, referred to herein as lateral surface 218, faces the external wall and bony capsule (not shown) of cochlea 115. It should be understood that the terms medial surface, medial direction, and the like, are generally used herein to refer to the surfaces, features and directions toward the center of cochlea 115, while the terms lateral surface, lateral direction, and the like, are generally used herein to refer to surfaces, features and directions toward the exterior of cochlea 115.

As would be appreciated by those of ordinary skill in the art, electrodes 212 may be disposed in a linear or non-linear array on or in carrier member 202, and are typically positioned on or in carrier member 202 so as to align with predetermined regions of tonotopically mapped cochlea 115 when implanted in cochlea 115. In alternative embodiments, electrodes 212 are implemented as described in U.S. Provisional Patent Applications 60/748,217, 60/748,273 and 60/748,314, which are hereby incorporated by reference herein.

In one embodiment, electrodes 212 are half-band electrodes disposed in or on medial surface 216 of carrier member 202. It should be appreciated, however, that any electrodes now or later developed suitable for a particular application may be used in alternative embodiments of the invention. For example, in one alternative embodiment, electrodes 212 are banded electrodes extending substantially around the circumference of carrier member 202. In another embodiment, electrodes 212 do not laterally extend to or around the edges of carrier member 202. Typically, each electrode 212 is arranged such that its exposed surface is substantially parallel to a longitudinal axis 224 of carrier member 202. It should be appreciated, however, that other locations and orientations may be implemented in alterative embodiments. It should further be appreciated that the quantity of electrodes 212 may vary from as few as one or two to as many as twenty-four or more.

In certain embodiments, at least one electrode 212 has a surface that is at least adjacent medial surface 216 of carrier member 202. Preferably, one or more electrodes 212 has a surface that is collocated with medial surface 216 of carrier member 202. In another embodiment, the surfaces of electrodes 212 are raised above or recessed into the surface 216 of carrier member 202. It should be appreciated, however, that any embodiment of electrodes 212 may be implemented.

In certain embodiments, electrodes 212 are manufactured from a biocompatible conductive material such as platinum, although other materials or combinations of materials may be used. In certain alternative embodiments electrodes 212 are coated with a biocompatible covering that does not interfere with the transfer of stimulation signals to cochlea 115.

A variety of surgical methods may be used to implant an electrode assembly in a recipient, including a mastoidectomy and facial recess approach, a transcanal approach, or a combination thereof, depending upon the particular recipient anatomy, recipient needs and surgeon's discretion. For ease of description, embodiments of the present invention will be described with reference to implantation using a facial recess approach.

Referring again to FIG. 1, in an implantation procedure utilizing the facial recess approach, electrode assembly 140 is inserted during an operation that usually takes between 2-3 hours, depending on the device to be implanted. An incision is made behind outer ear 101 to expose temporal bone 160. Temporal bone 160 consists of several segments (not shown) known as the squamous, the mastoid, the tympanic, the zygomatic and the petrous segment. Typically, traditional cochlear implants require the opening of the mastoid segment of temporal bone 160 which leads to middle ear 102.

Following the opening of the incision behind outer ear 101, a shallow recess is created in the mastoid to hold implanted receiver 132 and stimulator 134. Next, additional amounts of the mastoid are removed. By removing this additional portion of the mastoid, the surgeon opens an area known as the facial recess. The facial recess is a concave portion of the inner side of the mastoid bone that opens to middle ear 102, and inner ear 103. As the facial recess is opened, the surgeon is able to access middle ear 102 and inner ear 103.

The surgeon then prepares an opening in cochlea 115 to allow implantation of electrode assembly 140 into cochlea 115. The opening may be formed through round window 141, oval window 110, the promontory or through the apical turn of the cochlea. Electrode assembly 140 is then gently threaded into the shell-like structure of the cochlea. Depending in the type of implant used, the opening may either remain open to heal with scar tissue, or may be closed by the surgeon. The procedure is completed by closing the incision behind outer ear 101.

FIG. 3 illustrates a perspective view of the right side of a recipient showing the location of implantation of certain embodiments of the electrode assembly of the present invention in accordance with the facial recess approach. It should be appreciated, however, that embodiments of the present invention are equally applicable to other implantation methods. Directional arrows 330, 332, 334 and 336 illustrate general directions in relation to the recipient. Directional arrow 330 illustrates the inferior direction, and refers to a direction that is towards the feet of the recipient. Directional arrow 332 illustrates the posterior direction, and refers to a direction that is towards the back of the recipient's head. Directional arrow 334 illustrates the superior direction, and refers to a direction that is towards the top of the recipient's head. Directional arrow 336 illustrates the anterior direction, and refers to a direction that is towards the front of the recipient's head.

As illustrated in FIG. 3, facial recess 362 is positioned between the facial nerve 310 and the cord-tympani nerve 312. Facial nerve 310 is positioned posterior to facial recess 362, and cord-tympani nerve 312 is positioned anterior to facial recess 362. Visible behind facial recess 362 is round window 141 of cochlea 115. In some embodiments of the present invention, electrode assembly 200 is configured to be implanted through facial recess 362 and into round window 141.

An implanted electrode assembly, such as electrode assembly 140, may have a tendency to migrate out of cochlea 115 following implantation. This may be due to the materials used for the construction of the electrode assembly, as well as the bias of the electrode assembly. For example, as a straight electrode assembly is inserted into cochlea 115, and thereby forced into a spiraled configuration, the electrode assembly attempts to return to a straight configuration. The forces applied by the electrode assembly to return to a straight configuration may cause the electrode assembly to migrate out of the cochlea. Another cause of such migration out of cochlea 115 is the inadvertent pulling of the electrode assembly during subsequent steps of the surgery. Another potential cause is when the electrode assembly has a spring force which if not properly stabilized. The spring force may tend to pull the electrode assembly out over a long period of time.

Figure 4:
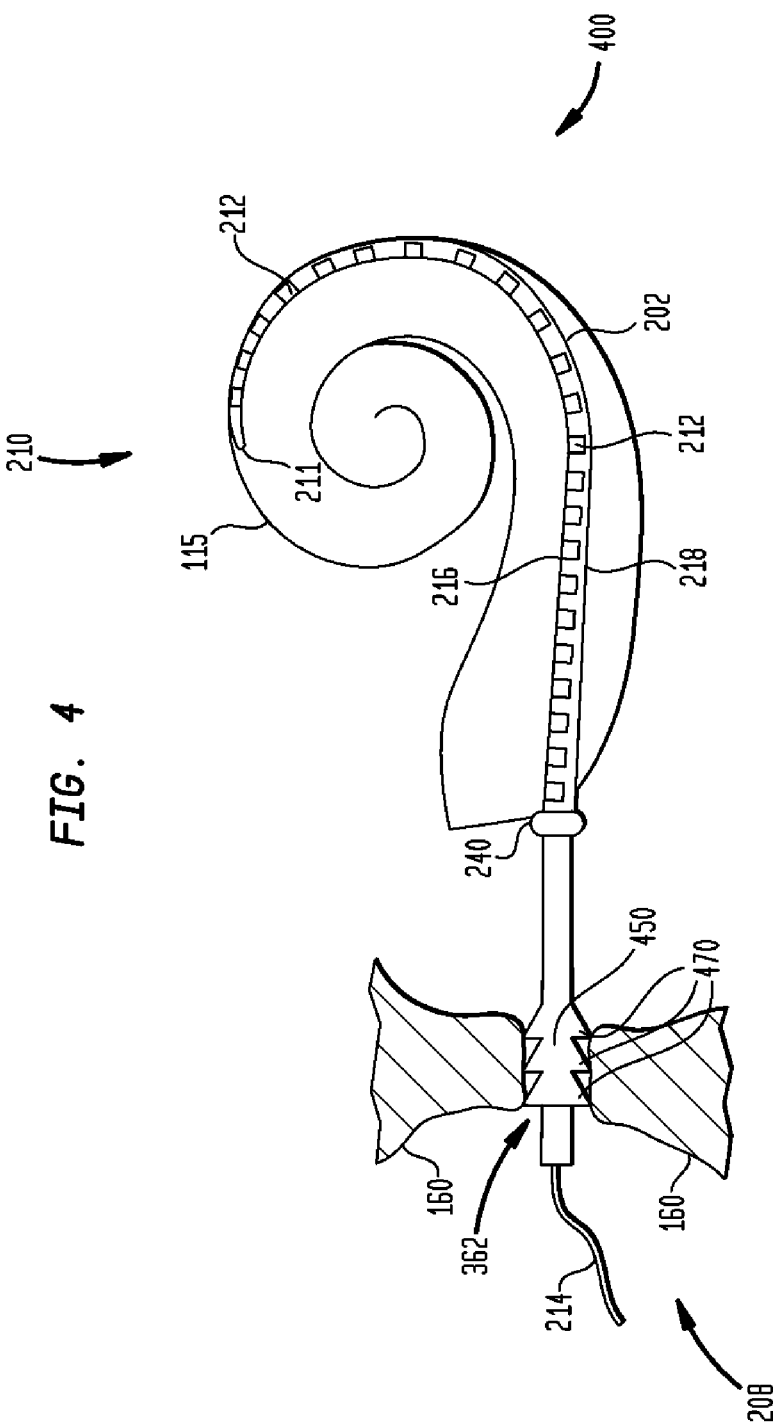
FIG. 4 is a side view of one embodiment of the electrode assembly illustrated in FIGS. 2A and 2B.

FIG. 4 is a side view of one embodiment of electrode assembly 140, referred to herein as electrode assembly 400, configured to reduce the ability of electrode assembly 400 to exit cochlea 115 following implantation. In FIG. 4, electrode assembly 400 is shown in an implanted position, and is viewed from an anterior direction of the recipient. Electrode assembly 400 comprises a carrier member 202, having proximal end 208 and distal end 210, terminating in tip 211. A plurality of spaced-apart electrodes 212 are disposed in carrier member 202 along medial surface 216 of carrier member 202. The opposing side of carrier member 202 is referred to herein as lateral surface 218. Lead 214 extends from proximal end 208.

Attached to or integral with carrier member 202 are stop member 240 as described with reference to FIGS. 2A and 2B, and fixation structure 450. Fixation structure 450 is positioned at or near proximal end 208 of carrier member 202 to substantially interact with at least a portion of the bone surrounding facial recess 362. In the specific embodiment shown in FIG. 4, fixation structure 450 comprises a series of circumferentially-extending projections 470. If circumferentially-extending projections 470 are viewed along a plane that extends longitudinally through fixation structure 450, each projection may have, for example, a substantially triangular cross-sectional shape.

In FIG. 4, circumferentially-extending projections 470 are dimensioned to extend from carrier member 202 to bone 160 surrounding facial recess 362. The above-noted tendency of electrode assembly 400 to exit cochlea 115 places pressure on fixation structure 450 to exit the recipient. However, the pressure from carrier member 202 causes circumferentially-extending projections 470 to further interact with bone 160. This interaction produces a longitudinal anchor force that substantially prevents longitudinal movement (that is, movement in a direction approximately parallel to the longitudinal axis of the device) of fixation structure 450 out of the recipient. This resulting longitudinal anchor force is a force along the longitudinal axis of electrode assembly 400 in the direction of cochlea 115. The longitudinal anchor force maintains fixation structure 450 in bone 160 thereby retaining carrier member 202 in a desired position in cochlea 115. In other words, the longitudinal anchor force prevents substantial longitudinal movement of carrier member 202 out of cochlea 115.

As noted, embodiments of electrode assembly 400 may include half-band electrodes. For optimal stimulation, an electrode assembly utilizing half-band electrodes is preferably maintained in a desired position and orientation within cochlea 115. However, due to certain aspects of the implantation procedure, a rotational force may be created on electrode assembly 400 that causes electrode assembly 400 to twist within cochlea 115. If electrode assembly 202 twists within cochlea 115, the half band electrodes will no longer be in a desired orientation for optimal stimulation. In such embodiments, fixation structure 450 may be configured to produce an additional anchor force that prevents rotation of electrode assembly 400 within cochlea 115. This additional anchor force is referred to herein as a rotational anchor force. As electrode assembly 400 attempts to twist within cochlea 115, the torque causes circumferentially-extending projections 470 to further interact with bone 160. This additional interaction produces a rotational anchor force that substantially prevents rotational movement of fixation structure 450. As a result of this rotational anchor force rotational movement substantial of carrier member 202 is also prevented.

In certain embodiments, fixation structure 450 comprises a flexible material having a diameter that is larger than facial recess 362. In such embodiments, during implantation, flexible fixation structure 450 is forced in facial recess 362 and is compressed therein. As fixation structure 450 attempts to exit cochlea 115, the compression of fixation structure 450 by bone 160 creates the longitudinal anchor force that prevents movement of fixation structure 450 out of cochlea 115. In such embodiments, fixation structure 450 may comprise a flexible component such as silicone, polyurethane, PTFE, etc.

In other embodiments, the longitudinal anchor force created by the interaction of fixation structure 450 and bone 160 may be the result of friction. As electrode assembly 400 attempts to exit cochlea 115, the friction between fixation structure 450 and bone 160 produces the longitudinal anchor force that prevents movement of electrode assembly 400. In certain embodiments, fixation structure 450 may have a rough or uneven surface that increases friction with bone 160.

As would be understood to those of ordinary skill in the art, the bone surrounding facial recess 362 is typically not a smooth surface, and likely has burrs and marks resulting from its interaction with surgical tools, as well due to the structural features of bone 160. For example, bone 160 naturally includes aerated sections that form openings in the bone. Such attributes of bone 160 tend to increase the friction between fixation structure 450 and bone 160. In further embodiments, the surface of bone 160 may be purposefully scored to further increase the friction with fixation structure 450.

Fixation structure 450 may comprise a flexible component as described above. In an alternative embodiment, fixation structure 450 may comprise a malleable material such as a metal or a hard plastic or a shape-memory material that changes shape upon heating to body temperature or other catalyst such has IR or UV light, to anchor itself into the recess in bone 160. In such embodiments fixation structure 450 may comprise materials such as titanium, platinum, stainless steel, chromium, nitinol, etc. In one particular embodiment, the shape-memory material comprises a shape-memory polymer.

FIGS. 5A-5H depict various embodiments of fixation structure 250 (FIGS. 2A, 2B) which may take advantage of the non-smooth surface of bone 160 to increase the longitudinal and/or rotational anchor forces created by the interaction of the two. For example, in certain embodiments, fixation structure 250 comprises non-smooth surfaces that may protrude into openings or burs within bone 160 to further engage bone 160. As the uneven surfaces of such fixation structures 250 protrude into openings in bone 160, the uneven surface interlocks with bone 160. This interlocking creates longitudinal anchor force that prevents substantial longitudinal movement of such embodiments of fixation structure 250 and thereby physically retaining carrier member 202 (FIGS. 2A, 2B) in a desired position in cochlea 115.

In alternative embodiments, fixation structure 250 may comprise a malleable material, as described above. In such embodiments, in addition to the friction force created between fixation structure 250 and bone 160, the pressure exerted on bone 160 by the malleable material may, over time, cause fixation structure 250 to cut into bone 160, causing fixation structure 250 to interlock with bone 160. This interlocking creates a longitudinal anchor force that prevents substantial longitudinal movement of such embodiments of fixation structure 250 thereby physically retaining carrier member 202 (FIGS. 2A, 2B) in a desired position in cochlea 115.

In further embodiments, fixation structure 250 may be configured or treated to facilitate the in-growth of bone 160 to fixation structure 250, further increasing the longitudinal and rotational anchor forces.

As would be appreciated by one of ordinary skill in the art, circumferentially-extending projections of embodiments of fixation structure 250 such as projections 470 of fixation structure 450 do not necessarily interact with bone 160 at all surfaces of bone 160. For example, fixation structure 450 may be positioned in facial recess 362 such that circumferentially-extending projections 470 interact with one, two, three or more surfaces of bone 160. Accordingly, in alternative embodiments, projections may not circumferentially extend around the entire perimeter of fixation structure 250.

Alternatively, fixation structure 250 may be made of a hydrogel material to expand and lock into the slot in the bone. Preferably, the expansion of such an embodiment of fixation structure 250 is controllable so that the timing of swelling is determined by the surgeon. This may be attained, for example, by pulling a "plug" on fixation structure 250 to let moisture reach the hydrogel, or by piercing an outer silicone casing of 250 to let moisture through.

The various embodiments of fixation structure 250 may also be constructed and arranged to prevent rotation of electrode assembly 200. As noted, such embodiments, fixation structure 250 interacts with bone 160 to produce a rotational anchor force. The rotational anchor force may be created by any manner described above. For example, a rotational anchor force may be created by friction between bone 160 and fixation structure 250, or by the interlocking of fixation structure 250 and bone 160.

Figure 5A:
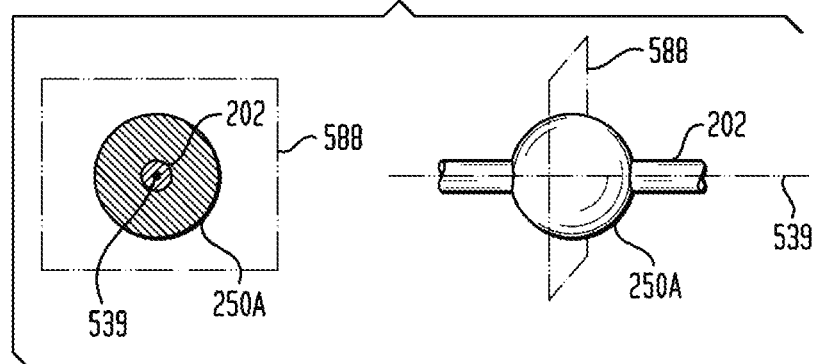
FIGS. 5A-5H are cross section and side views of the fixation structure illustrated in FIGS. 2A and 2B, in accordance with certain embodiments of the present invention.

FIGS. 5A-5H each illustrate cross-sectional and (left) (right) side views of different embodiments of fixation structure 250. FIG. 5A illustrates one alternative embodiment of fixation structure 250, referred to as fixation structure 250A. Fixation structure 250A has a generally spherical shape that substantially surrounds carrier member 202. As shown with reference to cross-sectional plane 588, spherical fixation structure 250A has an approximately circular cross section, with the center of spherical fixation structure 250A positioned on a longitudinal axis 539 extending through the center of carrier member 202. Spherical fixation structure 250A is dimensioned such that at least a portion of the outer surface of spherical fixation structure 450A is in contact with bone 160 following implantation of electrode assembly 200.

The interaction of bone 160 and spherical fixation structure 250A produces a longitudinal anchor force that substantially maintains fixation structure 250A in a desired location relative to bone 160. As fixation structure 250A is maintained in the desired location, carrier member 202 is, as noted, substantially prevented from longitudinal movement toward or away from cochlea 115. Also as described above, this longitudinal anchor force may be the result of several different interactions between spherical fixation structure 250A and bone 160. For example, in one embodiment, the longitudinal anchor force resulting from the interaction between spherical fixation structure 450A and bone 160 may be the result of friction between the two surfaces. However, as would be appreciated by one of ordinary skill in the art, fixation structure 250A may be configured to interact with bone 160 in any manner described herein to produce the longitudinal anchor force.

Figure 5B:
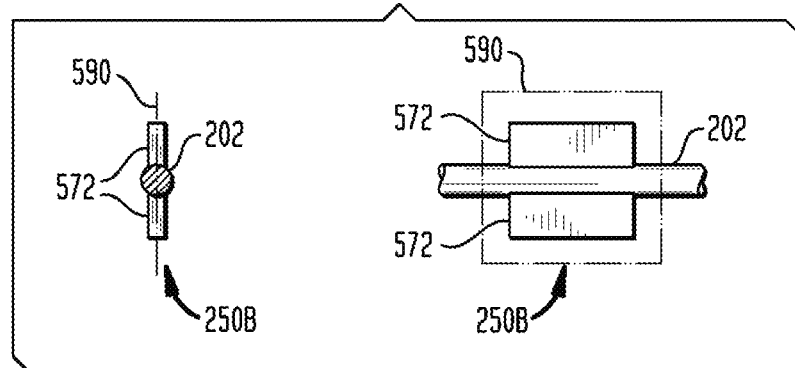

FIG. 5B illustrates another embodiment of fixation structure 250, referred to as fixation structure 250B. Fixation structure 250B comprises a pair of radially-extending projections 572. Radially-extending projections 572 are positioned, in this embodiment, approximately 180 degrees relative to each other and lie in a plane illustrated in FIG. 5B as plane 590. Plane 590 extends laterally and longitudinally through the center of carrier member 202. Viewing radially-extending projections 572 within plane 592, radially-extending projections 572 each have, in this example, a substantially rectangular cross section. Radially-extending projections 572 have a length that is parallel to carrier member 202 and a width that is perpendicular to carrier member 202, with the length being greater than the width. Radially-extending projections 572 are dimensioned to interact with bone 160 on opposing sides of carrier member 202.

The interaction of bone 160 and radially-extending projections 572 produces a longitudinal anchor force that substantially maintains fixation structure 250B in a desired fixed location relative to bone 160. As fixation structure 250B is maintained in the desired location, carrier member 202 is, as noted, substantially prevented from longitudinal movement toward or away from cochlea 115. Also as described above, this longitudinal anchor force may be the result of several different interactions between radially-extending projections 572 and bone 160. For example, in one embodiment, the longitudinal anchor force resulting from the interaction between radially-extending projections 572 and bone 160 may be the result of friction between the outer surface of radially-extending projections 572 that lies parallel to, but away from carrier member 202, and bone 160. In another embodiment, radially-extending projections 572 are configured to fit into the natural openings in bone 160 to maintain fixation structure 250B in a desired location. In still further embodiments, radially-extending projections 572 are comprised of a material that cuts into bone 160 to thereby maintain fixation structure 250B in a desired location. However, as would be appreciated by one of ordinary skill in the art, radially-extending projections 572 may be configured to interact with bone 160 in any manner described herein so as to produce the desired longitudinal anchor force.

In an alternative embodiment, radially-extending projections 572 may be flexibly biased so that they fold against carrier member 202 during insertion, and then radially extend after insertion. In one embodiment, this may be provided with shape memory material that extends upon heating to 37C. In another embodiment, a hydrogel may be incorporated into projections 572 to cause the extension. Such embodiments prevent radially-extending projections 572 from interfering with the surgeon's visibility during insertion.

Figure 5C:
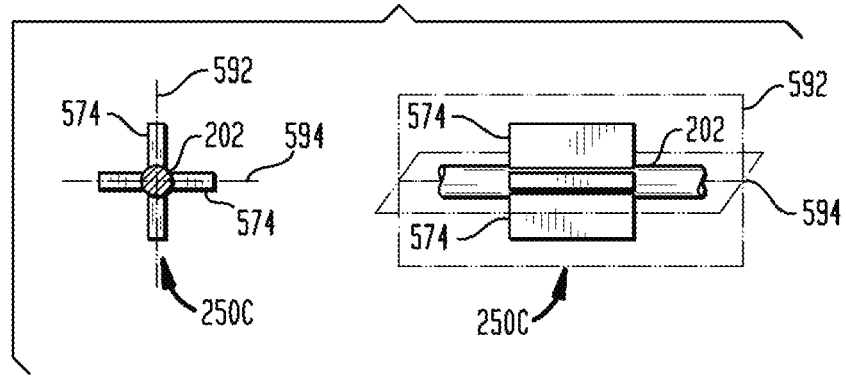

FIG. 5C illustrates another embodiment of fixation structure 250, referred to as fixation structure 2500. Fixation structure 250C comprises four radially-extending projections 574 each having an approximately quadrilateral shape. Radially-extending projections 574 are radially positioned around carrier member 202 so as to be spaced approximately 90 degrees relative to each other. One set of radially-extending projections 574 are positioned approximately 180 degrees from each other and lie in a plane illustrated in FIG. 5C as plane 592. Plane 592 extends longitudinally through the center of carrier member 202. A second set of radially-extending projections 574 are positioned 180 degrees from each other and lie in a plane illustrated in FIG. 5C as plane 594. Plane 594 extends longitudinally through the center of carrier member 202, but is substantially perpendicular to plane 592. Viewing radially-extending projections 574 within either plane 592 or plane 594, radially-extending projections 574 each have a substantially rectangular cross section with a length that is parallel to carrier member 202 and a width that is perpendicular to carrier member 202, wherein the length is greater than the width. Radially-extending projections 574 are dimensioned to provide contact with bone 160 at up to four separate locations surrounding carrier member 202 following implantation of electrode assembly 200.

The interaction of bone 160 and radially-extending projections 574 produces a longitudinal anchor force that substantially maintains fixation structure 250C in a desired location relative to bone 160. As fixation structure 250C is maintained in a desired location, carrier member 202 is securely positioned within cochlea 115 and is, as noted, prevented from longitudinal movement toward or away from cochlea 115. Also as described above, this longitudinal anchor force may be the result of several different interactions between radially-extending projections 574 and bone 160. For example, in one embodiment, the longitudinal anchor force resulting from the interaction between radially-extending projections 574 and bone 160 may be the result of friction between the outer surface of radially-extending projections 574 that lies parallel to, but away from carrier member 202, and bone 160. In another embodiment, radially-extending projections 574 are configured to fit into the natural openings in bone 160 to maintain fixation structure 250C in a desired location. In still further embodiments, radially-extending projections 574 are comprised of a material that slightly cuts into bone 160 to thereby maintain fixation structure 250C in a desired location. However, as would be appreciated by one of ordinary skill in the art, radially-extending projections 574 may be configured to interact with bone 160 in any manner described herein so as to produce the desired longitudinal anchor force.

Figure 5D:
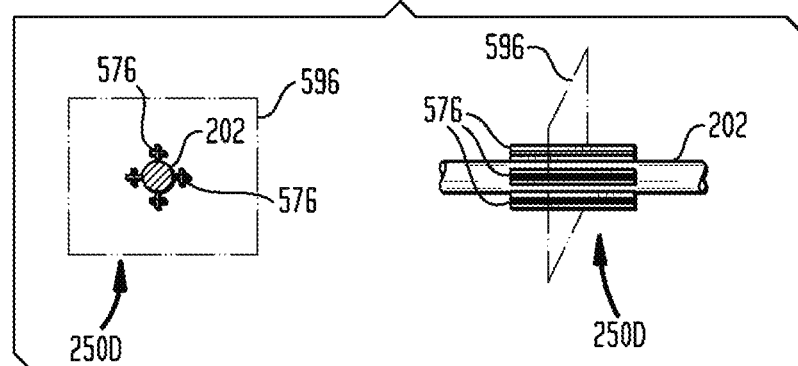

FIG. 5D illustrates another embodiment of fixation structure 250, referred to as fixation structure 250D. Fixation structure 250D comprises a plurality of radially-extending projections 576. In this exemplary embodiment, there are four (4) radially-extending projections 576 each radially positioned on carrier member 202 so as to be spaced approximately 90 degrees from one another. Viewing radially-extending projections 576 in a cross section plane shown in FIG. 5D as plane 596, each radially-extending projection 576 has an approximately cross-shaped cross section. Within plane 596, radially-extending projections 576 each comprise a first approximately rectangular central region extending away from carrier member 202. Extending from each of these rectangular central regions are two approximately square shaped regions. The square shaped regions extend from opposing sides of the central region substantially parallel to carrier member 202. As such, within plane 596 each radially-extending projection 576 has the noted cross-shaped cross section. Radially-extending projections 576 are dimensioned to interact with bone 160 at up to four separate locations surrounding carrier member 202 following implantation of electrode assembly 200. It should be appreciated, however, that more or less projections 576 may be implemented in alternative embodiments, with such projections been spaced apart by any distance and in any manner necessary to achieve a desired anchoring of fixation structure 250D with bone 160. For example, projections 576 may be longitudinally offset relative to each other, or have different longitudinal lengths.

The interaction of hone 160 and radially-extending projections 576 produces a longitudinal anchor force that substantially maintains fixation structure 250D in a desired location relative to bone 160. As fixation structure 250D is maintained in the desired location, carrier member 202 is securely positioned within cochlea 115 and is, as noted, substantially prevented from longitudinal movement toward or away from cochlea 115. Also as described above, this longitudinal anchor force may be the result of several different interactions between radially-extending projections 576 and bone 160. For example, in one embodiment the longitudinal anchor force resulting from the interaction between radially-extending projections 576 and bone 160 may be the result of friction between the outer surface of radially-extending projections 576 that lies parallel to, but away from carrier member 202, and bone 160. In another embodiment, radially-extending projections 576 are configured to fit into the natural openings in bone 160 to maintain fixation structure 250D in a desired location. In still further embodiments, radially-extending projections 576 are comprised of a material that cuts into bone 160 to thereby maintain fixation structure 250D in a desired location. However, as would be appreciated by one of ordinary skill in the art, radially-extending projections 576 may be configured to interact with bone 160 in any manner described herein so as to produce the desired longitudinal anchor force.

Figure 5E:
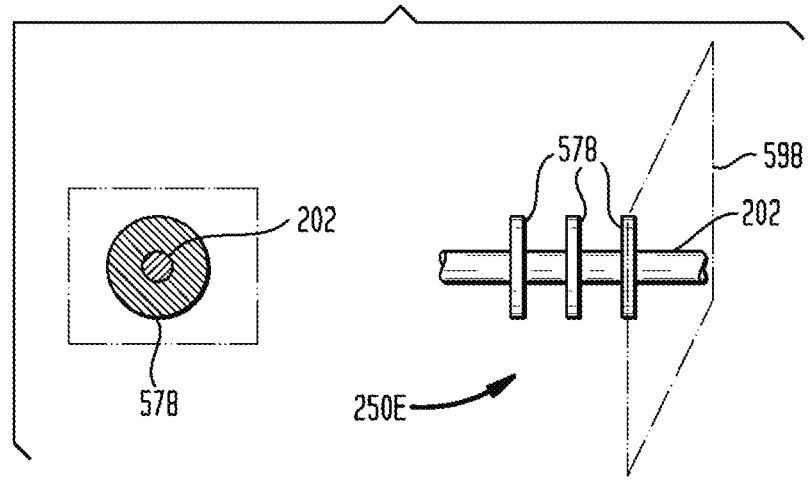

FIG. 5E illustrates another embodiment of fixation structure 250, referred to as fixation structure 250E. Fixation structure 250E comprises a series of longitudinally spaced disks each circumferentially-extending from carrier member 202. In this illustrative embodiment, fixation structure 250E comprises a series of three circumferentially-extending disks 578, although other quantities may be implemented. Following implantation of electrode assembly 200, a substantial portion of the outer circumference of each disk is configured to interact with bone 160.

The interaction of bone 160 and the outer surface of circumferentially-extending disks 578 produces a longitudinal anchor force that substantially maintains fixation structure 250E in a desired location relative to cochlea 115. As fixation structure 250E is maintained in the desired location, carrier member 202 is securely positioned within cochlea 115 and is, as noted, substantially prevented from longitudinal movement toward or away from cochlea 115. Also as described above, this longitudinal anchor force may be the result of several different interactions between circumferentially-extending disks 578 and bone 160. For example, in one embodiment the longitudinal anchor force resulting from the interaction between one or more circumferentially-extending disks 578 and bone 160 may be the result of friction between the outer surface of the circumferentially-extending disks and bone 160. In another embodiment, circumferentially-extending disks 578 are configured to fit into the natural openings in bone 160 to maintain fixation structure 250E in a desired location. In still further embodiments, circumferentially-extending disks 578 are comprised of a material that slightly cuts into bone 160 to thereby maintain fixation structure 450E in a desired location. However, as would be appreciated by one of ordinary skill in the art, circumferentially-extending disks 578 may be configured to interact with bone 160 in any manner described herein so as to produce the desired longitudinal anchor force.

Figure 5F:
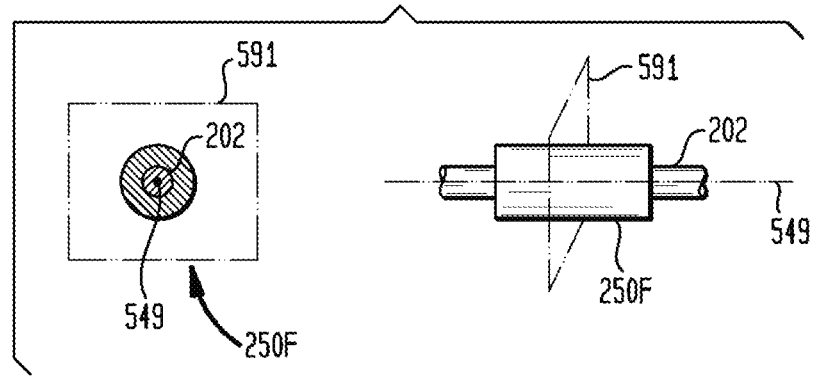

FIG. 5F illustrates another embodiment of fixation structure 250, referred to as fixation structure 250F. Fixation structure 250F comprises a cylindrical extension radially extending from carrier member 202. As shown with reference to cross sectional plane 591, cylindrical fixation structure 250F has an approximately circular cross section, with its center positioned on longitudinal axis 549 extending through the center of the length of carrier member 202. The diameter of cylindrical fixation structure 250F is substantially constant, although it may vary in alternative embodiments of the invention. Cylindrical fixation structure 250F is shaped and sized such that at least a portion of the outer surface of cylindrical fixation structure 250F is in contact with bone 160 following implantation of electrode assembly 400.

The interaction of bone 160 and cylindrical fixation structure 250F produces a longitudinal anchor force that substantially maintains fixation structure 250F in a desired fixed location relative to bone 160. As fixation structure 250F is maintained in the desired location, carrier member 202 is secured within cochlea 115 and is, as noted, substantially prevented from longitudinal movement toward or away from cochlea 115. Also as described above, this longitudinal anchor force may be the result of several different interactions between cylindrical fixation structure 450F and bone 160. For example, in one embodiment the longitudinal anchor force resulting from the interaction between cylindrical fixation structure 450F and bone 160 may be the result of friction between the two surfaces. However as would be appreciated by one of ordinary skill in the art, fixation structure 250F may be configured to interact with bone 160 in any manner described above with reference to FIG. 4 to produce the longitudinal anchor force.

Figure 5G:
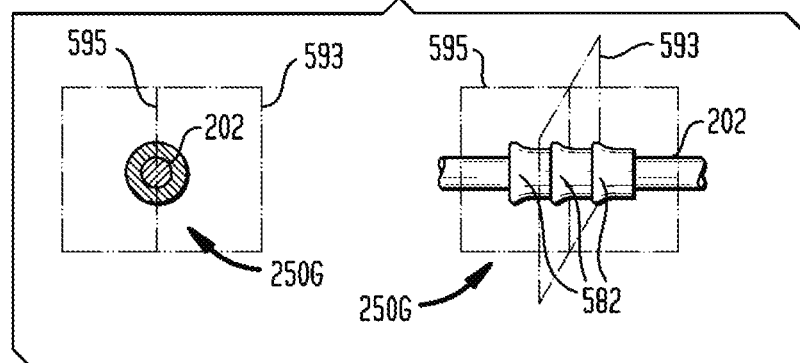

FIG. 5G illustrates another embodiment of fixation structure 250, referred to as fixation structure 250G. Fixation structure 250G comprises a series of circumferentially-extending projections 582. A plane 595 extends longitudinally through the center of carrier member 202. Viewing a circumferentially-extending projection within plane 595, each projection 582 has a cross section that includes three sides. The first side of the cross section is adjacent to, and parallel to carrier member 202. The other two sides of the cross section comprise a first arcuate slope joined to a second slope that is substantially perpendicular to carrier member 202 by a substantially rounded apex positioned apart from the first side of the cross section. Viewing a circumferentially-extending projection 582 within plane 593, the projection has an approximately circular cross section.

The interaction of bone 160 and circumferentially-extending projections 582 produces longitudinal anchor force that substantially maintains fixation structure 250G in a desired fixed location relative to cochlea 115. As fixation structure 250G is maintained in the desired location, carrier member 202 is, as noted, substantially prevented from longitudinal movement toward or away from cochlea 115. Also as described above, this longitudinal anchor force may be the result of several different interactions between circumferentially-extending projections 582 and bone 160. For example, in one embodiment the longitudinal anchor force resulting from the interaction between circumferentially-extending projections 582 and bone 160 may be the result of friction between the outer surface of circumferentially-extending projections 582 and bone 160. In another embodiment, portions of circumferentially-extending projections 582, particularly the rounded apex of each cross section, are configured to fit into the natural openings in bone 160 to maintain fixation structure 250G in a desired location relative to bone 160. In still further embodiments, circumferentially-extending projections 582 are comprised of a material that slightly cuts into bone 160 to thereby maintain fixation structure 250G in a desired location. However, as would be appreciated by one of ordinary skill in the art, circumferentially-extending projections 582 may be configured to interact with bone 160 in manner described above with reference to FIG. 4 so as to produce the desired longitudinal anchor three.

Figure 5H:
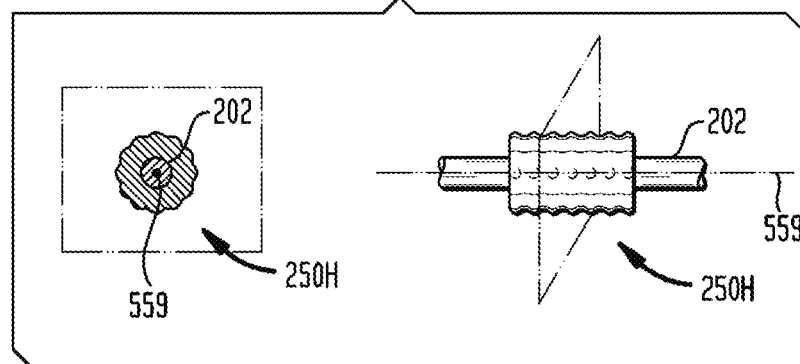

FIG. 5H illustrates another embodiment of fixation structure 250, referred to as fixation structure 250H. Fixation structure 250H comprises a generally cylindrical shape extending from carrier member 202. The diameter of cylindrical shaped fixation structure 450H varies along the length of carrier member 202 to produce a wavy-shaped surface of fixation structure 250H. As shown with reference to cross sectional plane 591, cylindrical fixation structure 250H has a generally circular cross section having its center positioned on the longitudinal axis 559 extending through the center of the length of carrier member 202, but with a diameter that varies. Cylindrical fixation structure 250H is shaped and sized such that at least a portion of the outer surface of cylindrical fixation structure 250H is in contact with bone 160 following implantation of electrode assembly 400.

The interaction of bone 160 and cylindrical fixation structure 250H produces a longitudinal anchor force that substantially maintains fixation structure 250H in a desired fixed location relative to cochlea 115. As fixation structure 450H is maintained in the desired location carrier member 202 is, as noted, prevented from longitudinal movement toward or away from cochlea 115. Also as described above, this longitudinal anchor force may be the result of several different interactions between cylindrical fixation structure 250H and bone 160. For example, in one embodiment the longitudinal anchor force resulting from the interaction between cylindrical fixation structure 250H and bone 160 may be the result of friction between the two surfaces. In another embodiment, portions of circumferentially-extending projections 582 are configured to fit into the natural openings in bone 160 to maintain fixation structure 250H in a desired location. However, as would be appreciated by one of ordinary skill in the art, fixation structure 250H may be configured to interact with bone 160 in any manner described above with reference to FIG. 4 to produce the longitudinal anchor force.

As would be appreciated by one of ordinary skill in the art, the embodiments described with reference to FIGS. 5A-5H are equally capable of producing the rotational anchor force to thereby prevent rotational movement of carrier member 202 within cochlea 115.

Figure 6:
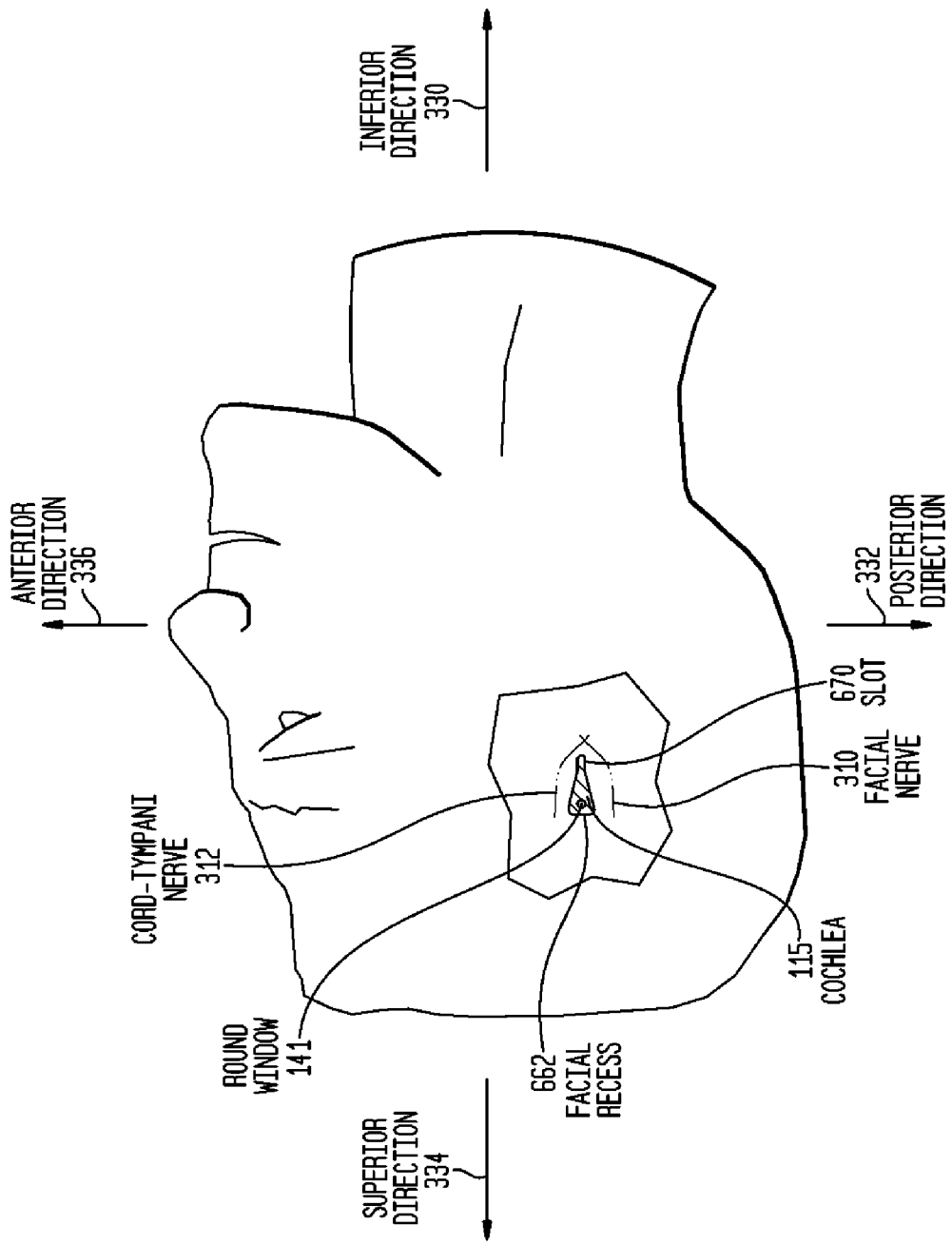
FIG. 6 is a perspective view of a recipient illustrating the location and orientation of the clithridiate opening utilized with embodiments of the present invention.

FIG. 6 is a perspective view of the right side of a recipient demonstrating the location of implantation of an electrode assembly in accordance with certain of the embodiments shown in FIGS. 7A-8D. As described above with reference to FIG. 3, facial recess 662 is located between the facial nerve 310 and the cord-tympani nerve 312. Facial nerve 310 is positioned posterior to facial recess 662, and cord-tympani nerve 312 is positioned anterior to facial recess 662. Visible behind facial recess 662 is round window 141 of cochlea 115.

In the embodiment shown in FIG. 6, facial recess 662 has a narrow slot 670 on the inferior side of facial recess 662. Slot 670 forms a channel running from facial recess 662 in an inferior direction. As shown in FIG. 6, facial recess 662 is a contiguous opening that has an approximately clithridiate, or key-hole shape.

Figure 7A:
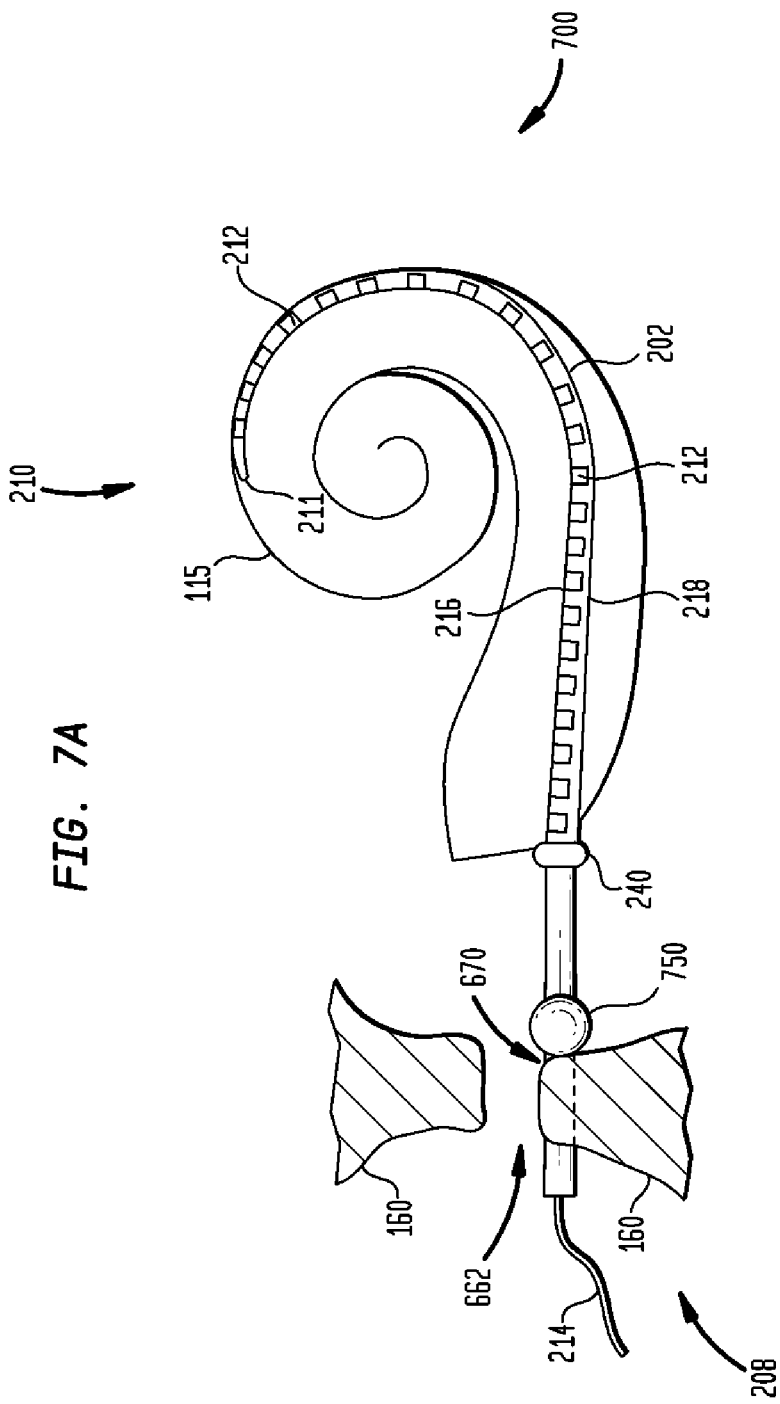
FIG. 7A is a side view of one embodiment of the electrode assembly illustrated in FIGS. 2A and 2B.

FIG. 7A is a side view of one embodiment of electrode assembly 140, referred to herein as electrode assembly 700, shown in an implanted configuration via facial recess 662 illustrated in FIG. 6. In FIG. 7A, cochlea 115 and electrode assembly 700 are viewed from the anterior direction of the recipient.

Electrode assembly 700 comprises a carrier member 202, having proximal end 208 and distal end 210, terminating in tip 211. A plurality of spaced-apart electrodes 212 mounted on or in carrier member 202 along medial surface 216 of carrier member 202. The opposing side of carrier member 202 is referred to herein as lateral surface 218. Lead 214 extends from proximal end 208 to stimulator unit 134 (FIG. 1).

Attached to or integral with carrier member 202 are stop member 240 as described herein with reference to FIGS. 2A and 2B, and fixation structure 750. Fixation structure 750 is positioned at or near proximal end 208 of carrier member 202 to substantially interact with at least a portion of the bone surrounding facial recess 362. Illustrative embodiments of fixation structure 750 are described below with reference to FIGS. 8A-8D.

As described above, in embodiments utilizing facial recess 362, a surgeon inserts electrode assembly 700 through bone 160, across middle ear 102 and into cochlea 115 through round window 141 until stop element 240 contacts cochlea 115. Stop element 240 is substantially similar as described above with reference to FIGS. 2A and 2B.

After stop element member 240 contacts cochlea 115, the surgeon positions proximal end 208 of carrier member 202 into slot 670 of facial recess 662. As shown in FIG. 7A, fixation structure 750 is positioned on carrier member 202 such that after placement of proximal end 208 into slot 670, fixation structure 750 contacts bone 160 surrounding slot 670.

As described above, an implanted electrode assembly has a tendency to exit cochlea 115 following implantation. In the illustrated embodiment, as electrode assembly 700 attempts to exit cochlea 115, fixation structure 750 is pressed against bone 160. As such, fixation structure 750 interacts with bone 160 and a longitudinal anchor force is exerted on electrode assembly 700 in the direction of cochlea 115. This longitudinal anchor force thereby securely locks carrier member 202 into a desired position within cochlea 115 by preventing if from exiting the cochlea. To remove carrier member 202 from cochlea 115, a surgeon may lift proximal end 208 of carrier member 202 from slot 670 and exit fixation structure 750 through facial recess 662.

Figure 7B:
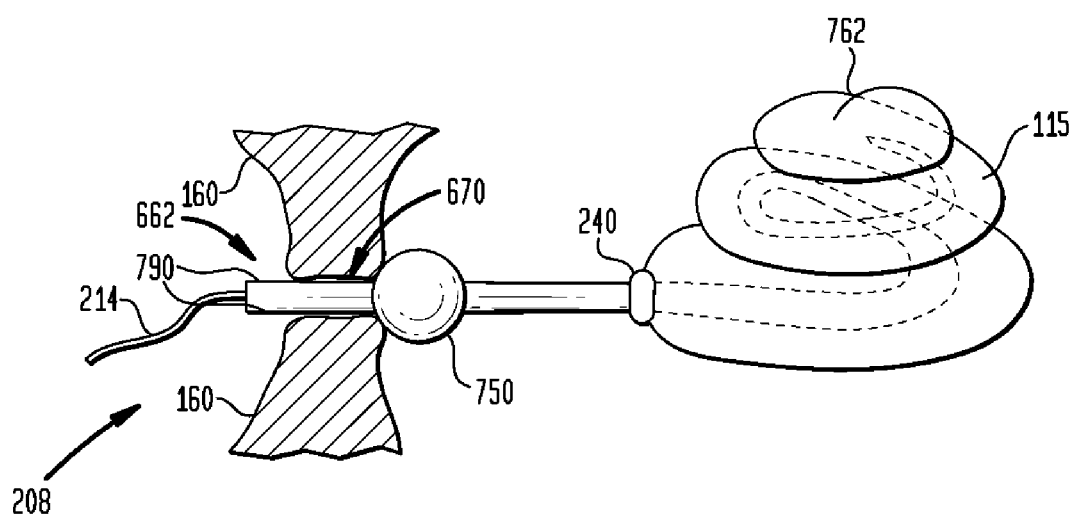
FIG. 7B is a side view of on embodiment of the electrode assembly illustrated in FIG. 7A.

FIG. 7B is an alternative view of the electrode assembly illustrated in FIG. 7A spiraling into cochlea 115. In FIG. 7B, electrode assembly 700 and cochlea 115 are viewed from a superior direction of the recipient. Cochlea 115 spirals to the apex 762 of cochlea 115.

As noted above, electrode assemblies in accordance with certain embodiments of the present invention include half-band electrodes. For optimal stimulation, an electrode assembly utilizing half-band electrodes is preferably maintained in both a desired position and orientation within cochlea 115. As such, in additional embodiments, carrier member 202 and fixation structure 750 may be configured to collectively lock electrode assembly 700 into both a desired position and orientation in cochlea 115. In such embodiments, proximal end 208 may comprise planar surfaces on at least two parallel edges of carrier member 202, shown in FIG. 7B as parallel planar surfaces 790. Proximal end 208 having surfaces 790 is placed into slot 670 with surfaces 790 each abutting and parallel to bone 160 that partially surrounds slot 670. Once placed within slot 670, if carrier member 202 would attempt to twist within cochlea 115, surfaces 790 would be forced against bone 160. The interaction of bone 160 and surfaces 790 produces a rotational anchor force that prevents axial rotation of carrier member 202.

FIGS. 8A-8D are cross section and side views of embodiments of a fixation structure 750 in accordance with embodiments of the present invention, as described with reference to FIGS. 7A and 7B. Specifically, the fixation structures shown in FIGS. 8A-8D may be utilized to lock carrier member 202 into cochlea 115.

Figure 8A:
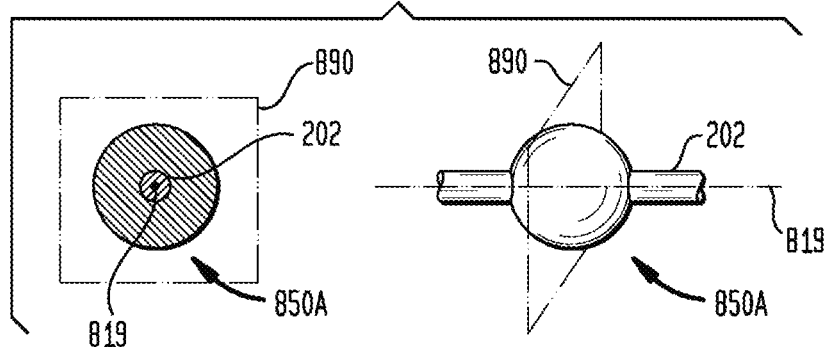
FIGS. 8A-8D are cross sectional and side views of embodiments of a fixation structure in accordance with certain embodiments of the present invention.

FIG. 8A illustrates one embodiment of fixation structure 750, referred to as fixation structure 850A. Fixation structure 850A has a generally spherical shape that substantially surrounds carrier member 202. As shown with reference to cross sectional plane 890, spherical fixation structure 850A has an approximately circular cross section, with the center of spherical fixation structure 850A positioned on the longitudinal axis 819 extending through the center of the length of carrier member 202. Spherical fixation structure 850A is dimensioned such that at least a portion of the outer surface of spherical shaped fixation structure 850A is in contact with bone 160 following implantation of electrode assembly 700. Any movement of carrier member 202 out of cochlea 115 is prevented by a longitudinal anchor force back towards cochlea 115 that is produced by the interaction of bone 160 and spherical shaped fixation structure 850A. Spherical shaped fixation structure 850A may be of any diameter that is sufficient to achieve desired interaction with bone 160. For example, spherical shaped fixation structure 850A may have a diameter that is larger than the width of slot 670.

Figure 8B:
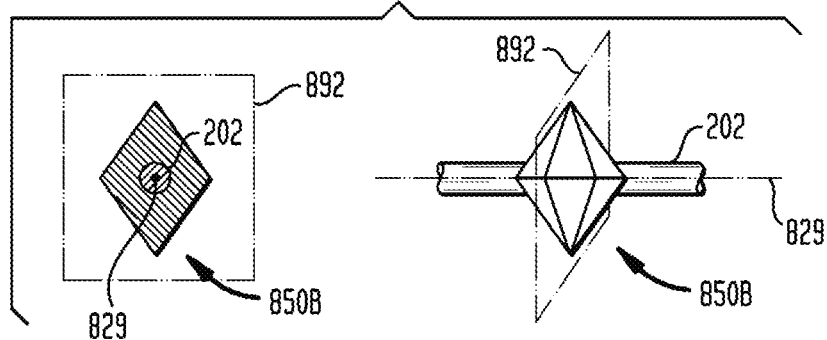

FIG. 8B illustrates another embodiment of fixation structure 750, referred to as fixation structure 850B. Fixation structure 850B has a diamond shape that substantially surrounds carrier member 202. As shown with reference to cross sectional plane 890, diamond shaped structure 850B has an approximately diamond cross section, and is positioned such that the longitudinal axis 829 extending through the center of the length of carrier member 202 also extends through the center of fixation structure 850B. Diamond shaped fixation structure 850B is dimensioned such that at least a portion of the outer surface of fixation structure 850B is in contact with bone 160 following implantation of electrode assembly 700. Any movement of carrier member 202 out of cochlea 115 is prevented by a longitudinal anchor force back towards cochlea 115 produced through the interaction of bone 160 and diamond shaped fixation structure 750B. Diamond shaped fixation structure 750B may have any dimensions that are sufficient to achieve desired interaction with bone 160. For example, the distance between the center of diamond shaped fixation structure 750B and any vertex of the diamond may be larger than the width of slot 670.

Figure 8C:
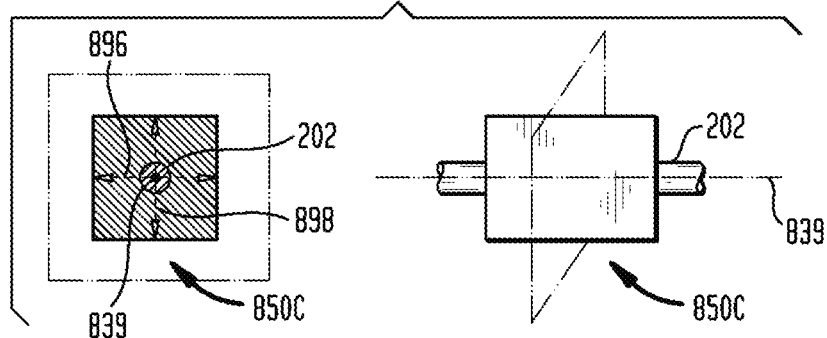

FIG. 8C illustrates a further embodiment of fixation structure 250, referred to as fixation structure 850C. Fixation structure 850C has a generally cube or cuboidal shape that substantially surrounds carrier member 202. As shown with reference to cross sectional plane 890, spherical fixation structure 850C has an approximately square cross section, with the center of spherical fixation structure 850C positioned the longitudinal axis 839 extending through the center of the length of carrier member 202. Fixation structure 850C is shaped and sized such that at least a portion of the outer surface of cuboidal fixation structure 850C is configured to be in contact with bone 160 following implantation of electrode assembly 400. Any movement of carrier member 202 out of cochlea 115 is prevented by a longitudinal anchor force back towards cochlea 115 produced through the interaction of bone 160 and cuboidal shaped fixation structure 850C. Cuboidal fixation structure 850C may be of any height 898 and width 896 that is sufficient to achieve desired interaction with bone 160. For example, cuboidal shaped fixation structure 850C may have a height 898 and width 896 that is larger than the width of slot 670.

Figure 8D:
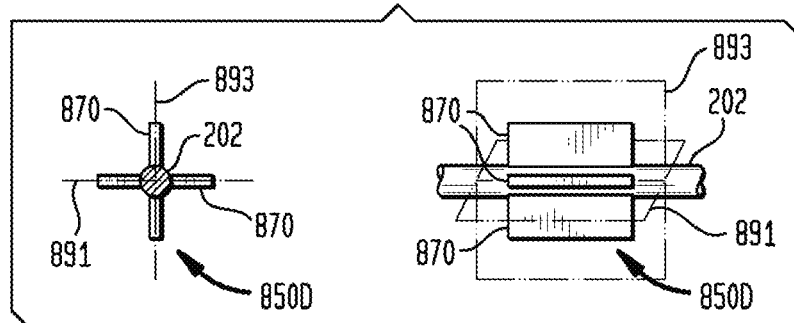

FIG. 8D illustrates a still other embodiment of fixation structure 250, referred to as fixation structure 850D. Fixation structure 850D comprises four radially-extending projections 870 each having an approximately quadrilateral shape. For example, in the illustrated embodiment, radially-extending projections 870 each have an approximately rectangular cross section as described below. Radially-extending projections 870 are positioned approximately 90 degrees from each other. One set of radially-extending projections 870 are positioned approximately 180 degrees from each other and lie in a plane illustrated in 8D as plane 893. A second set of radially-extending projections 870 are positioned 180 degrees from each other and lie in a plane illustrated in FIG. 8D as plane 891. Plane 891 extends longitudinally through the center of carrier member 202, but substantially perpendicular to plane 893. Viewing radially-extending projections 870 within either plane 893 or plane 891, radially-extending projections 870 each have an approximately rectangular cross section. Radially-extending projections 870 have a length that is parallel to carrier member 202 and a width that is perpendicular to carrier member 202, with the length being greater than the width. Radially-extending projections 870 are shaped and sized to provide contact with bone 160 at four separate locations surrounding carrier member 202 following implantation of electrode assembly 400. Any movement of carrier member 202 out of cochlea 115 is prevented by a longitudinal anchor force back towards cochlea 115 produced through the interaction of bone 160 and radially-extending projections 870. Radially-extending projections 870 have sufficient length and width to prevent carrier member 202 from exiting through slot 670.

As described above with reference to FIGS. 7A and 7B, the embodiments illustrated in FIGS. 8A-8D may be further modified to prevent rotation of carrier member 202.

As would be appreciated by one of ordinary skill in the art, fixation structure 750 may comprise any shape or element that serves to interact with bone 160 to prevent longitudinal movement of carrier member 202 out of cochlea 115. For example, fixation structure 750 may comprise any of the embodiments of fixation structure 450 illustrated in FIGS. 5A-5H. All of the embodiments illustrated in FIGS. 5A-5H, utilized as described with reference to FIGS. 7A and 7B, would serve to interact with the cochlea-side of bone 160 to lock carrier member 202 into cochlea 115. Similarly, other embodiments for fixation structure 750 may be envisioned that have not been illustrated herein.

As would be further appreciated, in certain embodiments fixation structure 750 may comprise flexible materials such as silicone, polyurethane, PTFE, rubber etc. In alternative embodiments, fixation structure may comprise a malleable material such as metals or hard plastics. Specifically, the fixation structure may comprise materials such as titanium, platinum, stainless steel, chromium, nitinol etc.

In other aspects of the present invention utilizing embodiments of fixation structure 750, a surgeon does not cut slot 670 into a recipient prior to implantation of electrode assembly 700. Rather, a surgeon may desire to implant a bracket in the recipient to interact with fixation structure 750. FIGS. 9A and 9B illustrate partially cross sectional views of a recipient that demonstrate the location of brackets implanted by a surgeon. The brackets can be formed of any material(s) and have any dimensions appropriate for the application. For example, in one embodiment, the bracket is a shape memory alloy that is heated to adopt the final desired shape.

As shown in FIG. 9A, a bracket 930A is implanted on the posterior side of facial recess 362. Bracket 930A shown in FIG. 9A comprises a metal plate that is attached to bone 160 of the recipient with a bone screw 932. Similarly, as shown in FIG. 9B, bracket 930B is also implanted on the posterior side of facial recess 362. In this illustrated embodiment, bracket 930B comprises a malleable wire bracket secured to bone 160 with screw 932.

As would be appreciated by one of ordinary skill in the art, bracket 930 may be implanted at any location around facial recess 362 such that it at least partially extends over facial recess 362 and so long as it does not interfere with any nerves near facial recess 362.

Figure 10:
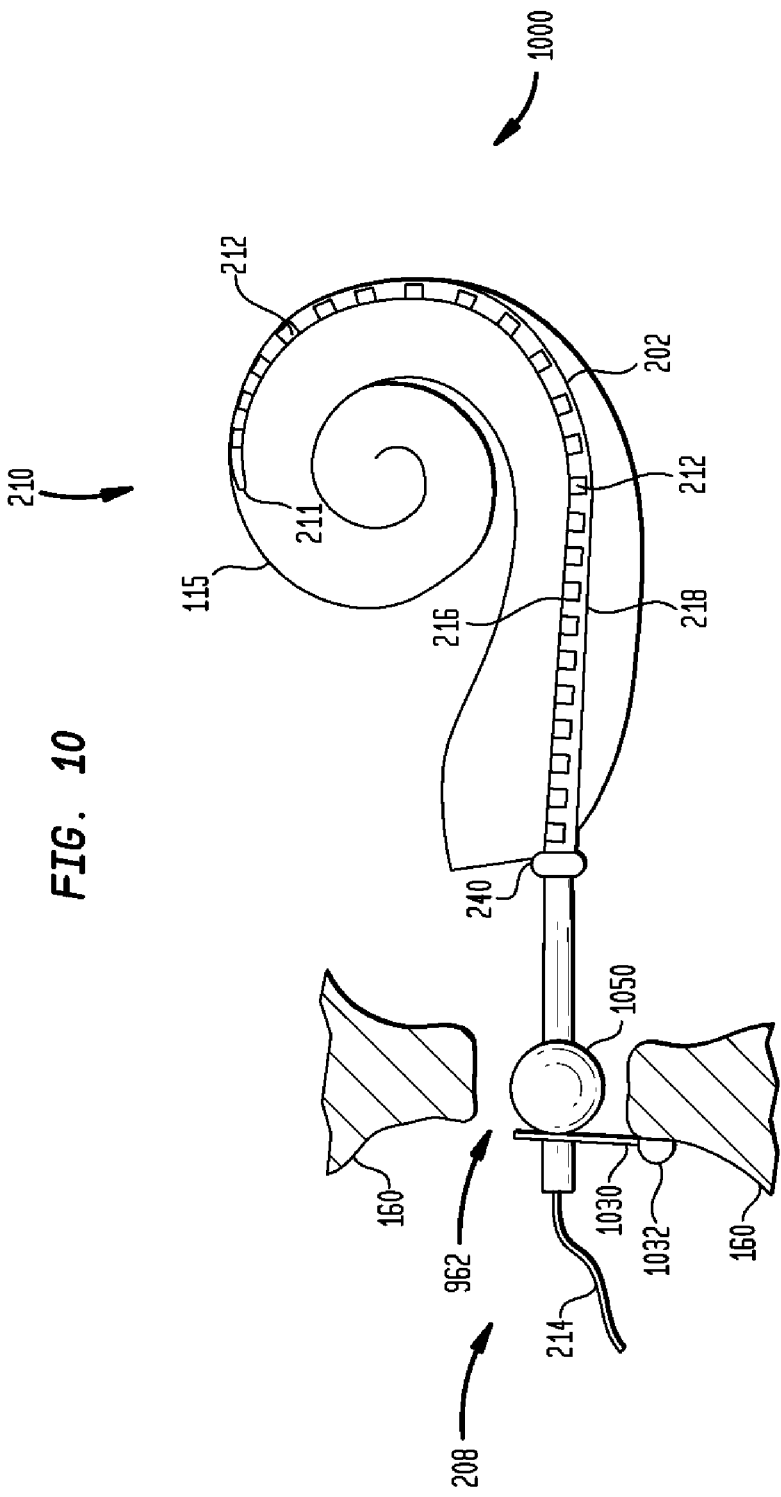
FIG. 10 is a side view of one embodiment of the electrode assembly illustrated in FIGS. 7A and 7B cooperating with a bracket.

FIG. 10 is a side view of one embodiment of the electrode assembly illustrated in FIGS. 7A and 7B, referred to as electrode assembly 1000, viewed from the anterior direction of the recipient. In the illustrated embodiment, electrode assembly 1000 interacts with a bracket 1030.

Electrode assembly 1000 comprises a carrier member 202, having proximal end 208 and distal end 210, terminating in tip 211. A plurality of spaced-apart electrodes 212 are mounted on or in carrier member 202 along the medial surface 216 of carrier member 202. Lead 214 extends from proximal end 208.

Attached to or integral with carrier member 202 are stop member 240 as described with reference to FIGS. 2A and 2B, and an embodiment of fixation structure 750, referred to herein as fixation structure 1050. Fixation structure 1050 is positioned at or near proximal end 208 of carrier member 202 to substantially interact with bracket 1030. As would be appreciated, fixation structure 1050 may comprise any fixation structure described above with reference to FIGS. 8A-8D and 5A-5F.

Prior to commencing implantation of electrode assembly 1000, a surgeon loosely attaches bracket 1030 to bone 160 with bone screw 1032. Bracket 1030 is swung away from facial recess 362 to allow the surgeon access to facial recess 362. As described above, in embodiments utilizing facial recess 362, a surgeon inserts electrode assembly 1000 through bone 160, across middle ear 102 and into cochlea 115 through round window 141, until stop element 240 contacts cochlea 115. Stop element 210 is substantially the same as described above. The surgeon then swings bracket 1032 back over facial recess 362 and secures bracket 1032 to bone 160 with screw 1032 to prevent movement of bracket 1032. The surgeon then positions proximal end 208 of carrier member 202 into receiving slot of bracket 1030 (not shown). Fixation structure 1050 is positioned on carrier member 202 such that after placement of proximal end 208 of carrier member 202 into the receiving slot of bracket 1030, fixation structure 1050 is in contact with bracket 1030.

As described above, an implanted electrode assembly may have a tendency to exit cochlea 115 following implantation. In the illustrated embodiment, as electrode assembly 1000 attempts to exit cochlea 115, fixation structure 1050 is pressed against bracket 1030. As such, fixation structure 1050 interacts with bone 160 and a longitudinal anchor force is exerted on electrode assembly 700 in the direction of cochlea 115. This longitudinal anchor force thereby locks carrier member 202 into a desired position within cochlea 115 by preventing an exit there from. To remove carrier member 202 from cochlea 115, the surgeon must lift proximal end 208 of carrier member 202 from bracket 1020 and exit fixation structure 750 through facial recess 362.

Furthermore, as would be appreciated, carrier member 202 may be modified as described above with reference to FIGS. 7A and 7B to interact with bracket 1030 to prevent rotation of electrode assembly 1000 within cochlea 115.

As would be understood by one of ordinary skill in the art, stop element 240 is not necessary for the present invention. In all embodiments stop element 240 may be omitted if desired.

As would be appreciated by one of ordinary skill the art, in the above embodiments the fixation structures may be positioned in or on the carrier member during manufacture of the electrode assembly. However, in alternative embodiments the fixation structure could be chosen by the surgeon at some time following manufacture. For example, a surgeon could choose the fixation structure that is believed to be the most fitting for the particular recipient during the implantation procedure. In such embodiments, the surgeon could prepare the insertion opening, and then fasten, attach, adhere or connect a properly shaped, sized and suited fixation structure to fit the prepared opening. It is also envisioned that a surgeon could attach the fixation structure prior to commencing the implantation procedure.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. For example, in the exemplary application above embodiments of the present invention have been described in the context of a cochlear implant. It should be appreciated, however, that embodiments of the present invention may be implemented in other medical devices now or later developed, including those that do not provide stimulation. Furthermore, embodiments of the present invention are not limited to any particular cochlear implant or cochlear implant function or modality. For example, embodiments of the present invention may be implemented in cochlear implants that perform operations to suppress tinnitus, provide vestibular treatments, and so on. It should further be appreciated that although in the above embodiments the present invention is implemented in connection with an electrode carrier member, embodiments of the present invention may be implemented in connection with other types of carrier members, other types of implantable devices and components, and so on. As another example, in the embodiments of the fixation structure such as those illustrated in FIGS. 5E and 5G, the structure is shown to be completely within the facial recess. It should be appreciated, however, that in other embodiments the fixation structure has a length that enables it to extends beyond the medial wall of the recess. This will allow the structure to expand and effectively create a lock against the medial wall of the facial recess, similar to the arrangement illustrated in FIG. 7B. It should further be appreciated that the reference structure in the recipient may not be bone as in the above exemplary applications. And, as noted above, it need not be biological. It may be man-made, or a combination of a man-made material injected into, applied to the surface of or otherwise used to treat a biological structure. Also, the rigidity of the reference structure may vary depending on, for example, the permissible movement of the controlled medical device; for example, the electrode carrier member in the above examples. Such changes and modifications are to be understood as included within the scope of the present invention as defined by the appended claims, unless they depart there from.

What is claimed is:

1. An electrode assembly, comprising:
an elongate carrier member including a distal end and a plurality of electrodes disposed along said carrier member proximal the distal end; and
an integrated fixation structure constructed and arranged to interact with a structure inside the head of a recipient of the electrode assembly when said carrier member is implanted in the recipient, wherein said interaction prevents substantial translation of said carrier member, wherein
the elongate carrier member is at least partially located in a cochlea of the recipient and is in at least a partially spiral configuration,
the electrode assembly is a straight electrode assembly, and
the fixation structure includes a plurality of circumferentially extending projections arrayed along a longitudinal axis of the electrode assembly proximate one another, which projections interface with the structure.

2. The electrode assembly of claim 1, wherein:
the fixation structure is located at a proximal end of the carrier member.

3. The electrode assembly of claim 1, wherein:
the fixation structure is configured to wedge in a passage in the structure and, as a result, resist movement of the carrier member out of the cochlea.

4. The electrode assembly of claim 1, wherein:
the elongate carrier member is under a tendency to back out of the cochlea owing to the elongate carrier member being in the at least partially spiral configuration and desirous to return towards the straight configuration, and the fixation structure resists said back out owing to the interface with the structure.

5. The electrode assembly of claim 1, wherein:
the fixation structure has locked the carrier member into the position in the cochlea.

6. The electrode assembly of claim 1, wherein:
an outermost profile of a cross-section of the fixation structure is concentric about a longitudinal axis of the electrode assembly.

7. The electrode assembly of claim 1, wherein:
the elongate carrier member is part of an electrode assembly that is connected to an internal receiver unit that transcutaneously receives power and coded signals from an external assembly.

8. A method, comprising:
obtaining an electrode array assembly including an electrode array and a lead assembly extending from the electrode array;
obtaining access to an internal location of a recipient proximate a cochlea of the recipient; and
inserting the electrode array into the cochlea, wherein
the action of inserting the electrode array into the cochlea is executed until a component of the electrode array assembly proximal of electrodes of the electrode array interfaces with bone of the recipient within the head of a recipient so that further insertion is significantly resisted.

9. The method of claim 8, wherein:
the interfacing with the bone of the recipient results in resistance to further insertion of the electrode array.

10. The method of claim 8, wherein:
the interfacing with the bone of the recipient is substantial interfacing with the bone of the recipient.

11. The method of claim 8, wherein:
the component is a circumferentially-extending component coaxial with a longitudinal axis of the electrode array proximate to the component and distal to the component.

12. The method of claim 8, wherein:
the electrode array is a straight electrode array; and
the action of inserting forces the array into a spiral configuration.

13. The method of claim 8, further comprising:
pulling of the electrode array assembly subsequent to insertion; and
an amount of the electrode array in the cochlea at the time that insertion of the electrode array into the cochlea is halted remains the same during the pulling.

14. The method of claim 8, further comprising:
pulling of the electrode array assembly subsequent to insertion; and
an amount of the electrode array in the cochlea at the time that insertion of the electrode array into the cochlea is halted remains the same during the pulling owing to fixation of the electrode array relative to the cochlea.

15. A method, comprising:
obtaining an electrode array assembly including an electrode array and a lead assembly extending from the electrode array;
obtaining access to an internal location of a recipient proximate a cochlea of the recipient in the head of the recipient;
inserting the electrode array into the cochlea; and
closing the access to the internal location, wherein
the electrode array is fixed to structure of the recipient at the internal location so as to resist migration out of the cochlea, and wherein
the method further includes wedging the electrode array into a passage through bone of the head of the recipient, which wedging causes the electrode array to be fixed to the structure.

16. The method of claim 15, wherein:
the electrode array is a straight electrode array that is in at least a partially coiled state owing to the spiral nature of the cochlea, and the coiled state induces migratory force onto the electrode array in a direction out of the cochlea which is resisted by the fixation to the structure.

17. The method of claim 15, wherein:
the electrode array has a spring force that imparts a tendency to pull the electrode array assembly out of the cochlea over a long period of time, which tendency is resisted by the fixation to structure at the internal location.

18. The method of claim 15, wherein:
the fixation to the structure reduces the ability of the electrode array to exit the cochlea following implantation.

19. The method of claim 15, wherein:
the electrode array assembly includes a plurality of wedge shaped portions; and
the method further comprises harnessing a force resulting from a tendency of the electrode array assembly to exit the cochlea so that the force causes at least one of the wedge shaped portions of the plurality of wedge shaped portions to further interact with the structure so that the interaction produces a longitudinal anchor force, which anchor force substantially prevents longitudinal movement of the electrode assembly out of the recipient.

* * * * *